(12) United States Patent
Onishi et al.

(10) Patent No.: US 11,064,895 B2
(45) Date of Patent: Jul. 20, 2021

(54) PULSE WAVE DETECTION DEVICE, IMAGE ANALYSIS DEVICE, AND BIOMETRIC INFORMATION GENERATION SYSTEM

(71) Applicant: Sharp Kabushiki Kaisha, Sakai (JP)

(72) Inventors: Junya Onishi, Sakai (JP); Yoshihisa Adachi, Sakai (JP); Tetsuya Okumura, Sakai (JP); Takashi Nunokawa, Sakai (JP); Rieko Ogawa, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 191 days.

(21) Appl. No.: 16/346,148

(22) PCT Filed: Nov. 6, 2017

(86) PCT No.: PCT/JP2017/039920
§ 371 (c)(1),
(2) Date: Apr. 30, 2019

(87) PCT Pub. No.: WO2018/088358
PCT Pub. Date: May 17, 2018

(65) Prior Publication Data
US 2020/0054222 A1 Feb. 20, 2020

(30) Foreign Application Priority Data
Nov. 10, 2016 (JP) .............................. JP2016-219887

(51) Int. Cl.
*A61B 5/021* (2006.01)
*A61B 5/024* (2006.01)
(Continued)

(52) U.S. Cl.
CPC ...... *A61B 5/02108* (2013.01); *A61B 5/02444* (2013.01); *G06K 9/00906* (2013.01); *G06T 7/0012* (2013.01); *A61K 38/42* (2013.01)

(58) Field of Classification Search
CPC ............ A61B 5/02444; A61B 5/02108; A61B 5/14542; A61B 2562/0219;
(Continued)

(56) References Cited

U.S. PATENT DOCUMENTS 10,687,706 B2 * 6/2020 Jeanne ................. A61B 5/4821
2008/0306372 A1 12/2008 Ohki et al.
(Continued)

FOREIGN PATENT DOCUMENTS

CN 102843962 A 12/2012
JP 2005-188969 A 7/2005
(Continued)

OTHER PUBLICATIONS

Hermeling, Evelien, et al. "Measurement of local pulse wave velocity: effects of signal processing on precision." Ultrasound in medicine & biology 33.5 (2007): 774-781. (Year: 2007).*
(Continued)

*Primary Examiner* — Pinalben Patel
(74) *Attorney, Agent, or Firm* — Keating & Bennett, LLP

(57) ABSTRACT

Pulse waves of a living body are detected with high accuracy. A pulse wave detection device includes a camera configured to capture an image of the living body a plurality of times through a first green filter and an infrared light filter having light transmission characteristics in a near-infrared light wavelength range within a wavelength range where a light absorption coefficient of oxidized hemoglobin is greater than a light absorption coefficient of reduced hemoglobin, and an image analysis unit configured to analyze a plurality of images of the living body captured by the camera and to detect the pulse waves of the living body. The image analysis unit is configured to detect the pulse waves by detecting a change in intensity of light in the near-infrared light wavelength range indicated by the plurality of images.

3 Claims, 18 Drawing Sheets

(51) Int. Cl.
    *G06K 9/00*     (2006.01)
    *G06T 7/00*     (2017.01)
    *A61K 38/42*     (2006.01)

(58) Field of Classification Search
    CPC ... A61B 5/02416; A61B 5/1032; A61B 5/318; A61B 5/7225; A61B 5/0077; A61B 5/352; A61B 5/0075; A61B 5/165; A61K 38/42; G06K 9/00013; G06K 2009/00939; G06K 9/00906; G06K 9/2018; G06K 9/00885; G06T 7/0012
    See application file for complete search history.

(56) References Cited

U.S. PATENT DOCUMENTS

| | | | |
|---|---|---|---|
| 2013/0018272 A1 | 1/2013 | Hori | |
| 2014/0058255 A1 | 2/2014 | Mase et al. | |
| 2014/0142441 A1 | 5/2014 | Fuke et al. | |
| 2014/0200423 A1* | 7/2014 | Eisen | A61B 5/14552 600/340 |
| 2014/0343383 A1* | 11/2014 | Sato | A61B 5/14551 600/324 |
| 2015/0019137 A1* | 1/2015 | Hamaguri | G01D 18/00 702/19 |
| 2015/0148687 A1 | 5/2015 | Kitajima et al. | |
| 2016/0300342 A1* | 10/2016 | Kikuchi | G06T 7/0012 |
| 2018/0000359 A1* | 1/2018 | Watanabe | A61B 5/0077 |
| 2018/0085010 A1 | 3/2018 | Jones et al. | |

FOREIGN PATENT DOCUMENTS

| | | |
|---|---|---|
| JP | 2008-301915 A | 12/2008 |
| JP | 2014-100244 A | 6/2014 |
| JP | 2014-198201 A | 10/2014 |
| JP | 2015-100432 A | 6/2015 |
| JP | 2016-103786 A | 6/2016 |
| WO | 2012/115220 A1 | 8/2012 |
| WO | 2016/159151 A1 | 10/2016 |
| WO | 2016/162980 A1 | 10/2016 |
| WO | 2016/163019 A1 | 10/2016 |

OTHER PUBLICATIONS

Official Communication issued in International Patent Application No. PCT/JP2017/039920, dated Jan. 23, 2018.

* cited by examiner

PULSE WAVE DETECTION DEVICE, IMAGE ANALYSIS DEVICE, AND BIOMETRIC INFORMATION GENERATION SYSTEM

TECHNICAL FIELD

The following disclosure relates to a pulse wave detection device and an image analysis device configured to detect pulse waves of a living body, and a biometric information generation system configured to generate biometric information of the living body on the basis of the pulse waves of the living body detected by the pulse wave detection device.

BACKGROUND ART

Pulse wave detection devices configured to detect pulse waves that refer to waveforms representing blood vessel beats associated with blood ejection of the heart are known. Biometric information, such as stress levels and blood pressure, can be obtained from the pulse waves detected by the above-mentioned pulse wave detection device.

A contact type pulse wave detection device is known as a pulse wave detection device. However, with a contact style pulse wave detection device, it is difficult to accurately detect the pulse waves because a subject to be measured becomes conscious of the measurement and deformation of the blood vessel occurs due to a measurement point of the subject to be measured making contact with the pulse wave detection device.

A non-contact pulse wave detection device capable of solving the problem described above is known, and is disclosed, for example, in PTL 1. In the pulse wave detection device disclosed in PTL 1, an image of a subject to be measured is captured with a camera, a position of a pulse wave detection region in the face of the subject to be measured in the image is calculated from the image, and then the pulse waves are detected in the above detection region.

In the pulse wave detection device of PTL 1, three types of light receiving elements of red (R), green (G), and blue (B) are mounted in the camera; pulse waves are detected using time series data of measures of central tendency of two wavelength components, which are an R component and a G component having different light absorption characteristics of blood, among the three types of wavelength components included in images captured by the camera, that is, the R component, the G component and a B component. In other words, in the pulse wave detection device of PTL 1, pulse waves are detected using the intensity of light in the visible light wavelength range.

CITATION LIST

Patent Literature

PTL 1: JP 2014-198201 A (published on Oct. 23, 2014)

SUMMARY OF INVENTION

Technical Problem

However, in the pulse wave detection device of PTL 1, the pulse waves are detected using the intensity of light in the visible light wavelength range as discussed above. In a case where the intensity of light in the visible light wavelength range is used to detect pulse waves, since a transmitting depth of the visible light inside a living body is shallow, only pulse waves of capillary vessels in a surface of the subject to be measured can be detected. As a result, there is a problem in the pulse wave detection device of PTL 1 that the pulse waves cannot be detected with high accuracy.

In addition, in a case that the subject to be measured moves, there is also a problem that the accuracy of detecting the pulse waves is lowered.

A pulse wave detection device and an image analysis device according to an aspect of the present disclosure have been conceived in view of the problems described above, and an object thereof is to accurately detect pulse waves of a living body.

Solution to Problem

To solve the above problems, a pulse wave detection device according to an aspect of the present disclosure is a pulse wave detection device configured to detect a pulse wave of a living body by analyzing an image obtained by capturing the living body, the pulse wave detection device including: an imaging unit configured to capture an image of the living body a plurality of times through a first filter having light transmission characteristics in a near-infrared light wavelength range within a wavelength range where a light absorption coefficient of oxidized hemoglobin is greater than a light absorption coefficient of reduced hemoglobin; and an image analysis unit configured to analyze a plurality of images of the living body captured by the imaging unit and to detect the pulse wave of the living body. The image analysis unit is configured to detect the pulse wave by detecting a change in intensity of light in the near-infrared light wavelength range indicated by the plurality of images.

To solve the above problems, an image analysis device according to an aspect of the present disclosure is an image analysis device configured to detect a pulse wave of a living body by analyzing an image obtained by capturing the living body, the image analysis device including: an acquisition unit configured to acquire a plurality of images obtained by capturing the living body through a first filter having light transmission characteristics in a near-infrared light wavelength range within a wavelength range where a light absorption coefficient of oxidized hemoglobin is greater than a light absorption coefficient of reduced hemoglobin; and an image analysis unit configured to analyze the plurality of images of the living body acquired by the acquisition unit and to detect the pulse wave of the living body. The image analysis unit is configured to detect the pulse wave by detecting a change in intensity of light in the near-infrared light wavelength range indicated by the plurality of images.

To solve the above problems, an image analysis device according to an aspect of the present disclosure is an image analysis device configured to detect a pulse wave of a living body by analyzing an image obtained by capturing the living body, the image analysis device including: an image analysis unit configured to detect a pulse wave of the living body by analyzing an image obtained by capturing the living body; and a correction unit configured to correct the pulse wave detected by the image analysis unit on the basis of a motion of the living body detected by a motion sensor configured to detect the motion of the living body.

Advantage Effects of Invention

According to an aspect of the present disclosure, an effect of accurately detecting pulse waves of a living body is achieved.

BRIEF DESCRIPTION OF DRAWINGS

FIG. 5A is a graph showing the correlation of an integral value LF, FIG. 5B is a graph showing the correlation of an integral value HF, and FIG. 5C is a graph showing the correlation of a value of LF/HF.

DESCRIPTION OF EMBODIMENTS

Embodiments of the present disclosure will be described as follows with reference to the drawings. Although, in each of the embodiments below, a pulse wave detection device and an image analysis device configured to detect pulse waves of a person from an image obtained by capturing the person are described, the present disclosure is not limited thereto. In other words, a pulse wave detection device and an image analysis device configured to detect pulse waves of a living body other than a person (any living body having a heart) from a moving picture obtained by capturing the stated living body, are also included in the scope of the present disclosure. Note that the pulse wave refers to a waveform representing a beat of a blood vessel associated with blood ejection of the heart.

First Embodiment

Figure 1:
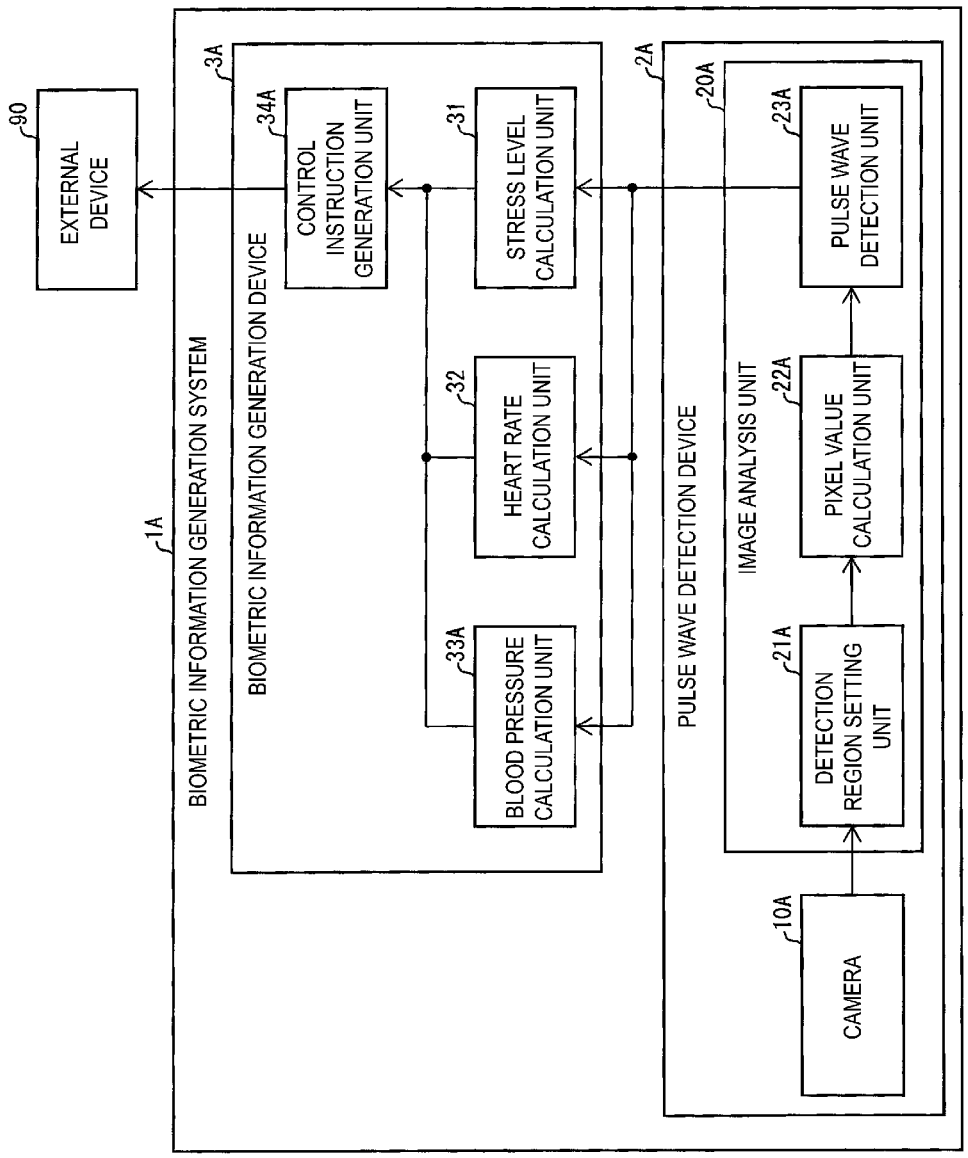
FIG. 1 is a block diagram illustrating a configuration of a main portion of a biometric information generation system according to a first embodiment of the present disclosure.

A biometric information generation system 1A according to a first embodiment of the present disclosure will be described in detail with reference to FIGS. 1 to 6.
Configuration of Biometric Information Generation System 1A The configuration of the biometric information generation system 1A will be described with reference to FIG. 1. FIG. 1 is a block diagram illustrating the configuration of a main portion of the biometric information generation system 1A.

Figure 2:
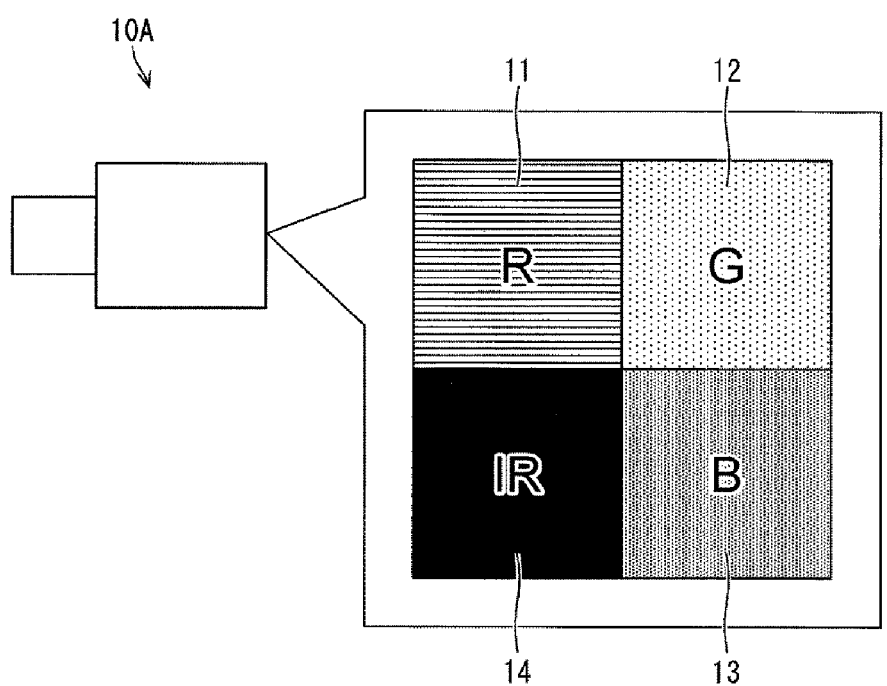
FIG. 2 is a schematic diagram illustrating a configuration of a camera included in the biometric information generation system.

As illustrated in FIG. 1, the biometric information generation system 1A includes a pulse wave detection device 2A and a biometric information generation device 3A.
Pulse Wave Detection Device 2A As illustrated in FIG. 1, the pulse wave detection device 2A includes a camera (imaging unit, imaging device) 10A and an image analysis unit (image analysis device) 20A.
Camera 10A The camera 10A will be described with reference to FIG. 2. FIG. 2 is a schematic diagram illustrating the configuration of the camera 10A.

As illustrated in FIG. 2, the camera 10A includes an image sensor (not illustrated) including a plurality of light receiving elements, and each light receiving element is provided with any of a red filter 11, a first green filter (first filter, second filter) 12, a blue filter 13, and an infrared light filter (first filter) 14. The camera 10A detects intensity (luminance) of light having passed through each of the red filter 11, the first green filter 12, the blue filter 13, and the infrared light filter 14, and generates a captured image. Each pixel in the captured image is formed by the light receiving elements each provided with any of the four types of filters described above.

Figure 3:
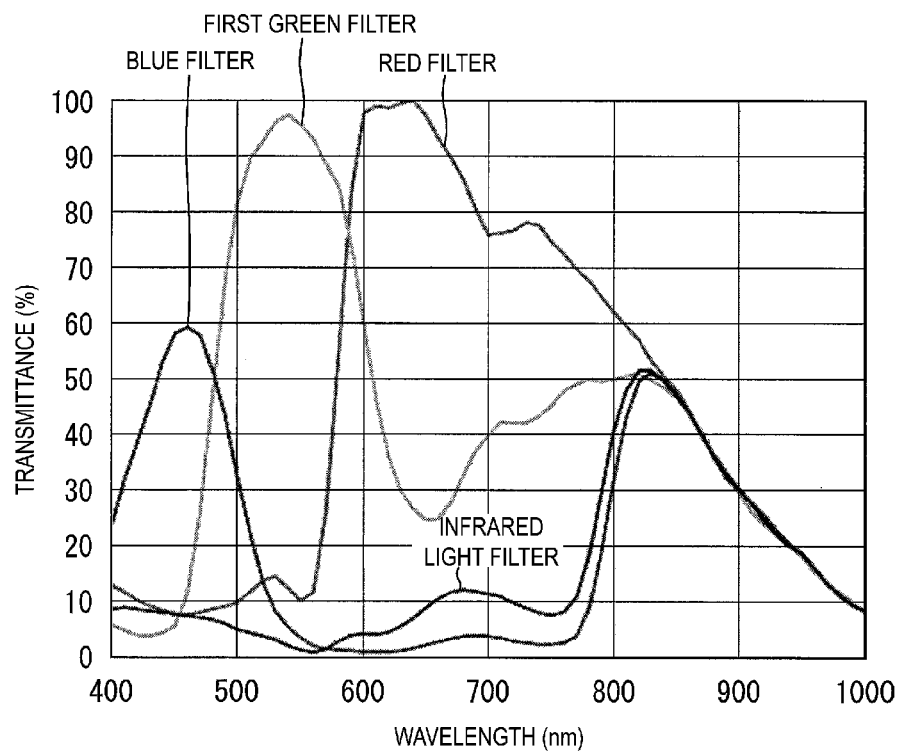
FIG. 3 is a graph showing light transmittance of a red filter, a first green filter, a blue filter, and an infrared light filter included in the camera.

Transmission characteristics (sensitivity characteristics) of the red filter 11, the first green filter 12, the blue filter 13, and the infrared light filter 14 will be described with reference to FIG. 3. FIG. 3 is a graph showing light transmittance of each of the red filter 11, the first green filter 12, the blue filter 13, and the infrared light filter 14. As shown in FIG. 3, the red filter 11 transmits the light in a red visible light wavelength range from about 600 nm to about 700 nm. The first green filter 12 transmits the light of a wavelength from about 500 nm to about 600 nm in a green visible light wavelength range and the light of a wavelength equal to or longer than about 805 nm in a near-infrared range. The blue filter 13 transmits the light of a wavelength from about 400 nm to about 500 nm in a blue visible light wavelength range. The infrared light filter 14 transmits the light of a wavelength equal to or longer than about 805 nm in the near-infrared range.

The camera 10A captures an image of an imaging target subject (living body) a plurality of times at a predetermined time interval on the basis of the intensity of the light having passed through the red filter 11, the intensity of the light having passed through the first green filter 12, and the intensity of the light having passed through the blue filter 13 and the infrared light filter 14, and outputs, to the image analysis unit 20A, a plurality of captured images generated as a result of the above capturing. In the following description, the camera 10A outputs a moving picture including a plurality of captured images to the image analysis unit 20A.

Image Analysis Unit 20A

The image analysis unit 20A detects pulse waves of a living body by analyzing a plurality of captured images included in a moving picture outputted from the camera 10A. The image analysis unit 20A may detect pulse waves using only part of the plurality of captured images (frames) included in the moving picture. As illustrated in FIG. 1, the image analysis unit 20A includes a detection region setting unit (acquisition unit) 21A, a pixel value calculation unit 22A, and a pulse wave detection unit 23A.

The detection region setting unit 21A acquires a moving picture of the living body outputted from the camera 10A (that is, the detection region setting unit 21A functions as an acquisition unit configured to acquire a plurality of images outputted from the camera 10A) and sets a detection region for detecting pulse waves in each of the captured images included in the moving picture. Note that the detection region needs to be selected from a region in which the skin of the living body is captured in the captured image. This is because the pulse wave is detected using a temporal change in the skin color of the subject to be measured.

Figure 4:
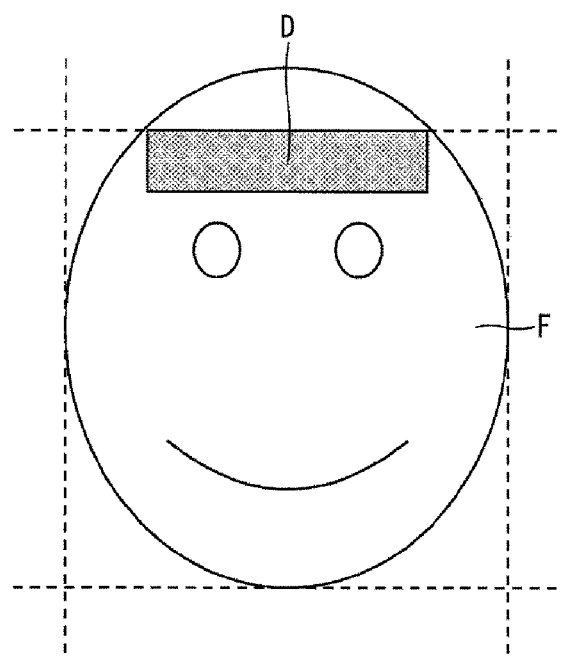
FIG. 4 is a diagram for explaining a setting of a detection region by a detection region setting unit included in the biometric information generation system.

FIG. 4 is a diagram for explaining the setting of the detection region by the detection region setting unit 21A. Specifically, as illustrated in FIG. 4, the detection region setting unit 21A first detects a facial region F of the living body for each prescribed frame of the moving picture of the living body outputted from the camera 10A. Known techniques can be used for the detection of the facial region F of the living body. Next, the detection region setting unit 21A sets a forehead region D as a detection region in the detected facial region F of the living body. In a case where the forehead region D is set as a detection region, a width from one-fifth to four-fifths of the facial region F from the left, and a region from 0 to one-fifth of the facial region F from the top may be referred to as the detection region. A region of the nose or cheek may be set other than the forehead region D as a detection region. Since there are arteries in the forehead, nose and cheek, and the forehead, nose, and cheek are regions easy to be detected in a case that the face of the living body faces the camera 10A, it is preferred to use them as a detection region. The neck may be a detection region in a case that the living body faces laterally with respect to the camera 10A.

The pixel value calculation unit 22A uses pixel values (gray-scale values) of respective colors (R, G, B, and IR (Infrared)) for representing each of pixels included in the captured image to calculate an arithmetic value of the pixel value of respective colors in the detection region (for example, the forehead region D). The arithmetic value is a value obtained by performing a predetermined arithmetic operation on the pixel values of a plurality of pixels included in the detection region in the captured image, and is also a value for reflecting a size of the pixel value of the pixel included in the detection region. The pixel value calculation unit 22A may calculate, for example, an average (average pixel value) of the pixel values of respective colors in the forehead region D as an arithmetic value of the pixel value in the forehead region D. The pixel value calculation unit 22A may calculate an arithmetic value of the pixel value in the forehead region D in the following manner: for example, statistical values are calculated in which the weight of the pixel values of the pixels near the center of the forehead region D is increased while the weight of the pixel values of the pixels separated from the center of the forehead region D is decreased, and then the calculated statistical values are taken as the above-mentioned arithmetic value. In the following description, the pixel value calculation unit 22A calculates the average pixel value of respective colors in the forehead region D as an arithmetic value of the pixel value in the forehead region D.

The pixel value calculation unit 22A calculates the average pixel value of frames for a predetermined amount of time (for example, 30 seconds) in the moving picture in order to obtain a temporal change of the average pixel value. The pixel value calculation unit 22A outputs the calculated average pixel value of respective colors to the pulse wave detection unit 23A.

Figure 18:
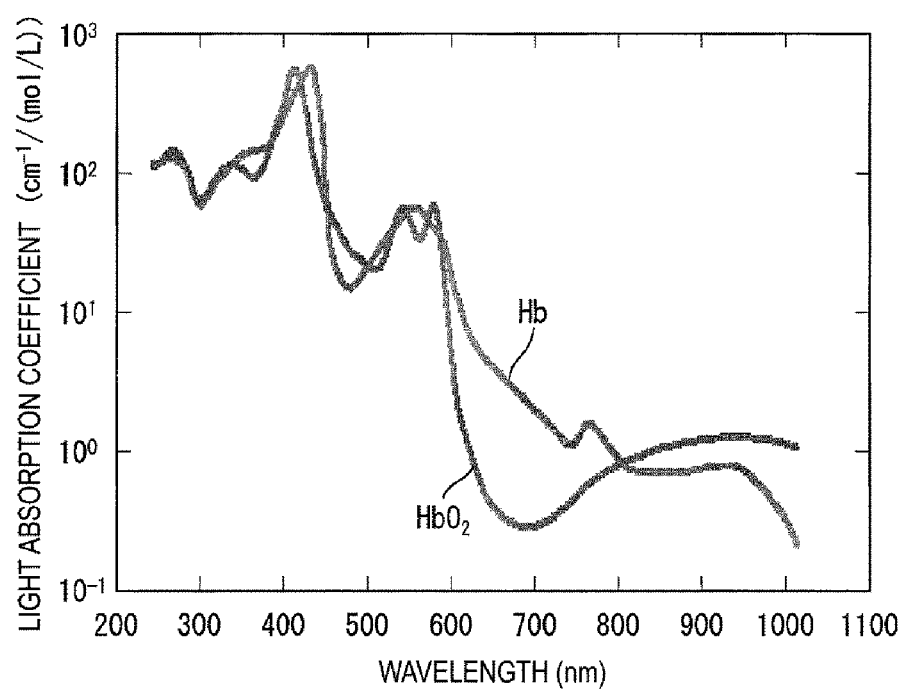
FIG. 18 is a graph showing a light absorption coefficient of each of oxidized hemoglobin and reduced hemoglobin.

Absorption of light by oxidized hemoglobin and reduced hemoglobin contained in the blood of a living body will be described with reference to FIG. 18. FIG. 18 is a graph showing a light absorption coefficient of oxidized hemoglobin and reduced hemoglobin. As illustrated in FIG. 18, in the wavelength ranges from 453 nm to 499 nm, 529 to 546 nm, 569 to 584 nm, and 805 nm to 1300 nm, the light absorption coefficient of oxidized hemoglobin is greater than that of reduced hemoglobin.

Accordingly, the average pixel value calculated on the basis of the intensity of light having passed through the first green filter 12 having light transmission characteristics in the wavelength ranges from 529 to 546 nm, 569 to 584 nm, and 805 nm to 1300 nm, has information on the concentration of oxidized hemoglobin in the blood of the living body. Likewise, the average pixel value calculated on the basis of the intensity of light having passed through the infrared light filter 14 having light transmission characteristics in the wavelength range from 805 nm to 1300 nm, which is a near-infrared range, also has information on the concentration of oxidized hemoglobin in the blood of the living body.

The pulse wave detection unit 23A calculates the pulse waves of the living body by detecting a change in the average pixel value of respective colors having been calculated by the pixel value calculation unit 22A. As described above, of the average pixel values in respective colors calculated by the pixel value calculation unit 22A, the average pixel value calculated on the basis of the intensity of the light having passed through the first green filter 12 or the infrared light filter 14 has information on the concentration of oxidized hemoglobin in the blood of the living body. Thus, the pulse wave detection unit 23A calculates the pulse waves of the living body on the basis of a change in the concentration of the oxidized hemoglobin.

Specifically, the pulse wave detection unit 23A first performs independent component analysis on the average pixel value of respective colors calculated by the pixel value calculation unit 22A, and extracts the same number (i.e., four) of independent components as that of the colors. Next, the pulse wave detection unit 23A uses a digital bandpass filter from 0.75 to 3.0 Hz with respect to the four extracted independent components to remove both a low frequency component and a high frequency component. Next, the pulse wave detection unit 23A performs fast Fourier transformation on the four independent components from which the low frequency component and the high frequency component have been removed, and calculates a frequency power spectrum of each of the independent components. Next, the pulse wave detection unit 23A calculates a peak value at 0.75 to 3.0 Hz of the calculated frequency power spectrum of each of the independent components, and detects, as pulse waves, the independent component having a peak with the highest peak value among the peak values of the independent components. The pulse wave detection unit 23A outputs the detected pulse waves to the biometric information generation device 3A.

In a case where a variation in the average pixel value calculated by the pixel value calculation unit 22A is large with respect to time, the pulse wave detection unit 23A may perform detrending on the average pixel values of respective colors (see IEEE TransBiomed Eng, 2002 February; 49(2): 172-175), and may perform the independent component analysis on the average pixel values of respective colors after having removed the above variation.

It can also be said that the image analysis unit 20A (the detection region setting unit 21A, the pixel value calculation unit 22A, and the pulse wave detection unit 23A) functions as an image analysis device configured to detect pulse waves of a living body by analyzing an image obtained by capturing the living body.

Biometric Information Generation Device 3A

The biometric information generation device 3A generates biometric information on a living body on the basis of the pulse waves detected by the pulse wave detection device 2A. In addition, the biometric information generation device 3A generates a control instruction for an external device (another device) 90 on the basis of the generated biometric information. As illustrated in FIG. 1, the biometric information generation device 3A includes a stress level calculation unit 31, a heart rate calculation unit 32, a blood pressure calculation unit 33A, and a control instruction generation unit 34A.

The stress level calculation unit 31 calculates a stress level of the living body on the basis of the pulse waves outputted from the pulse wave detection device 2A. Note that the "stress" in the present embodiment means the balance of activity of the sympathetic nerve and parasympathetic nerve. Specifically, a situation in which the sympathetic nerve is active as compared with the parasympathetic nerve is referred to as a "stressed state". On the other hand, a situation in which the parasympathetic nerve is active as compared with the sympathetic nerve is referred to as a "relaxed state".

Specifically, the stress level calculation unit 31 first detects a pulse wave peak from the pulse waves outputted from the pulse wave detection device 2A. Next, the stress level calculation unit 31 performs fast Fourier transformation at a period between a time at which a certain peak is detected and a time at which a peak next to the certain peak is detected, and calculates a power spectrum for a frequency. Next, the stress level calculation unit 31 calculates each of an integral value LF of the power spectrum at 0.04 to 0.15 Hz and an integral value HF of the power spectrum at 0.15 to 0.4 Hz in the calculated frequency power spectrum. Next, the stress level calculation unit 31 calculates a value obtained by dividing the integral value LF by the integral value HF (a value of LF/HF), and outputs the calculated value of LF/HF to the control instruction generation unit 34A.

Note that the integral value LF is an index indicating the degree of activity of the sympathetic nerve, and the integral value HF is an index indicating the degree of activity of the parasympathetic nerve. It is also known that the value of LF/HF being small (low) indicates the living body being in a relaxed state, while the value of LF/HF being large (high) indicates the living body being in a stressed state.

Figure 5A:
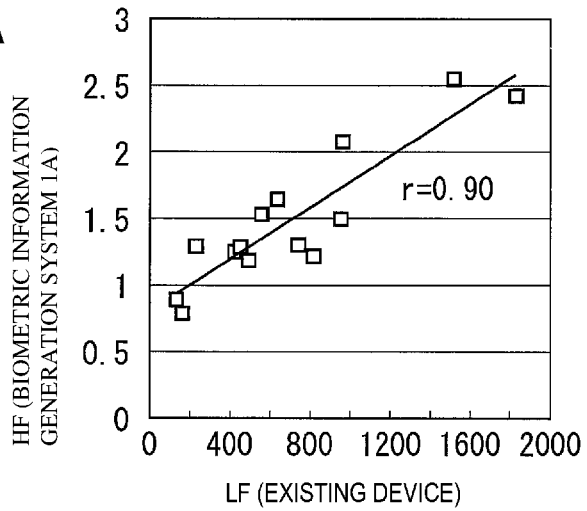
FIGS. 5A to 5C are graphs each showing correlation between a stress level calculated by the biometric information generation system and a stress level calculated by an existing device, where
Figure 5B:
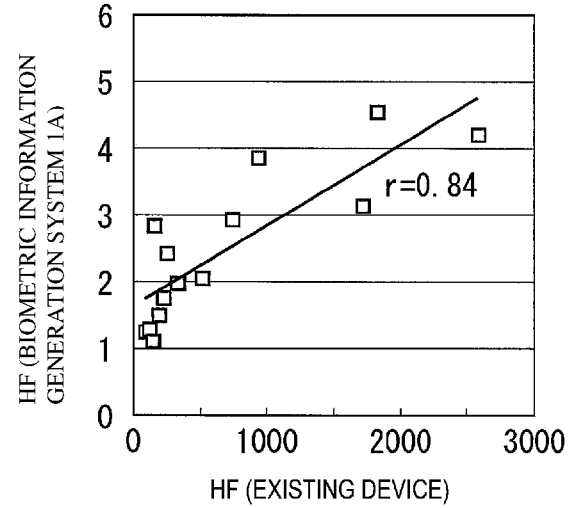
Figure 5C:
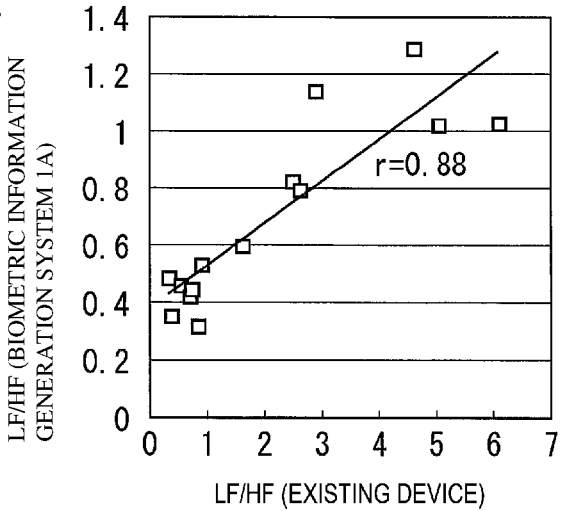

Here, the correlations between the integral value LF, the integral value HF and the value of LF/HF calculated by the biometric information generation system 1A of the present embodiment and the integral value LF, the integral value HF and the value of LF/HF calculated by an existing device configured to calculate pulse waves by making a detector in contact with a fingertip, will be described with reference to FIGS. 5A to 5C. FIGS. 5A to 5C are graphs each showing the correlation between the stress level calculated by the biometric information generation system 1A and the stress level calculated by the existing device, where FIG. 5A is a graph showing the correlation of the integral value LF, FIG. 5B is a graph showing the correlation of the integral value HF, and FIG. 5C is a graph showing the correlation of the value of LF/HF. As shown in FIGS. 5A to 5C, it can be understood that high correlations are obtained between the integral value LF, the integral value HF and the value of LF/HF calculated by the biometric information generation system 1A and the integral value LF, the integral value HF and the value of LF/HF calculated by the existing device.

The heart rate calculation unit 32 calculates a heart rate of the living body on the basis of the pulse waves outputted from the pulse wave detection device 2A. Specifically, the heart rate calculation unit 32 calculates the heart rate of the living body by counting the number of peaks in the pulse waves outputted from the pulse wave detection device 2A for a predetermined time (for example, 30 seconds). Next, the heart rate calculation unit 32 outputs the calculated heart rate of the living body to the control instruction generation unit 34A.

The blood pressure calculation unit 33A calculates blood pressure of the living body on the basis of the pulse waves outputted from the pulse wave detection device 2A. Specifically, the blood pressure calculation unit 33A first derives an acceleration pulse wave by differentiating twice the pulse waves outputted from the pulse wave detection device 2A. Next, the blood pressure calculation unit 33A specifies an "a" wave to an "e" wave from the derived acceleration pulse wave, and calculates each feature quantity from the "a" to "e" waves (specifically, the amplitude of the "a" to "e" waves, the ratios of the amplitude of the b wave to "e" wave to the amplitude of the "a" wave, and time intervals from the "a" wave to the "b" wave to "e" wave). It is known that each of the above-described feature quantities is correlated with a pulse wave velocity, and it is known that there is a correlation between a pulse wave velocity and blood pressure. In other words, there is a correlation between each of the feature quantities and blood pressure. Thus, in advance, data of each of the feature quantities and blood pressure data are acquired, and then a calculation formula for the blood pressure is created by performing, for example, a multiple regression analysis using these data. Then, the blood pressure calculation unit 33A calculates the blood pressure of the living body by giving the feature quantities to the above-mentioned calculation formula. Next, the blood pressure calculation unit 33A outputs the calculated blood pressure of the living body to the control instruction generation unit 34A.

The control instruction generation unit 34A generates a control instruction for the external device 90 on the basis of the biometric information outputted from the stress level calculation unit 31, the heart rate calculation unit 32, and the blood pressure calculation unit 33A. Examples of the external device 90 can include an electronic device such as a robot, television, personal computer, or air-conditioner. In the case where the external device 90 is a robot, the control instruction generation unit 34A issues a control instruction for the robot to cause the robot to give a speech or gestural motion such that the user can be relaxed, in response to the biometric information of the user. In the case where the external device 90 is a television or a personal computer, the control instruction generation unit 34A issues a control instruction for the television or the personal computer to cause the television or the personal computer to output an image or sound such that the user can be relaxed, in accordance with the biometric information of the user. In the case where the external device 90 is an air-conditioner, the control instruction generation unit 34A issues a control instruction for the air-conditioner to cause the air conditioner to adjust the temperature, air quantity, and wind direction in response to the biometric information of the user.

It is sufficient that the control instruction generation unit 34A generates a control instruction for the external device 90 on the basis of at least one of the biometric information of the stress level of the user outputted from the stress level calculation unit 31, the heart rate of the user outputted from the heart rate calculation unit 32, and the blood pressure of the user outputted from the blood pressure calculation unit 33 A, and it is not absolutely necessary to generate a control instruction on the basis of all of the biometric information of the stress level, heart rate, and blood pressure.

Operations of Biometric Information Generation System 1A

Figure 6:
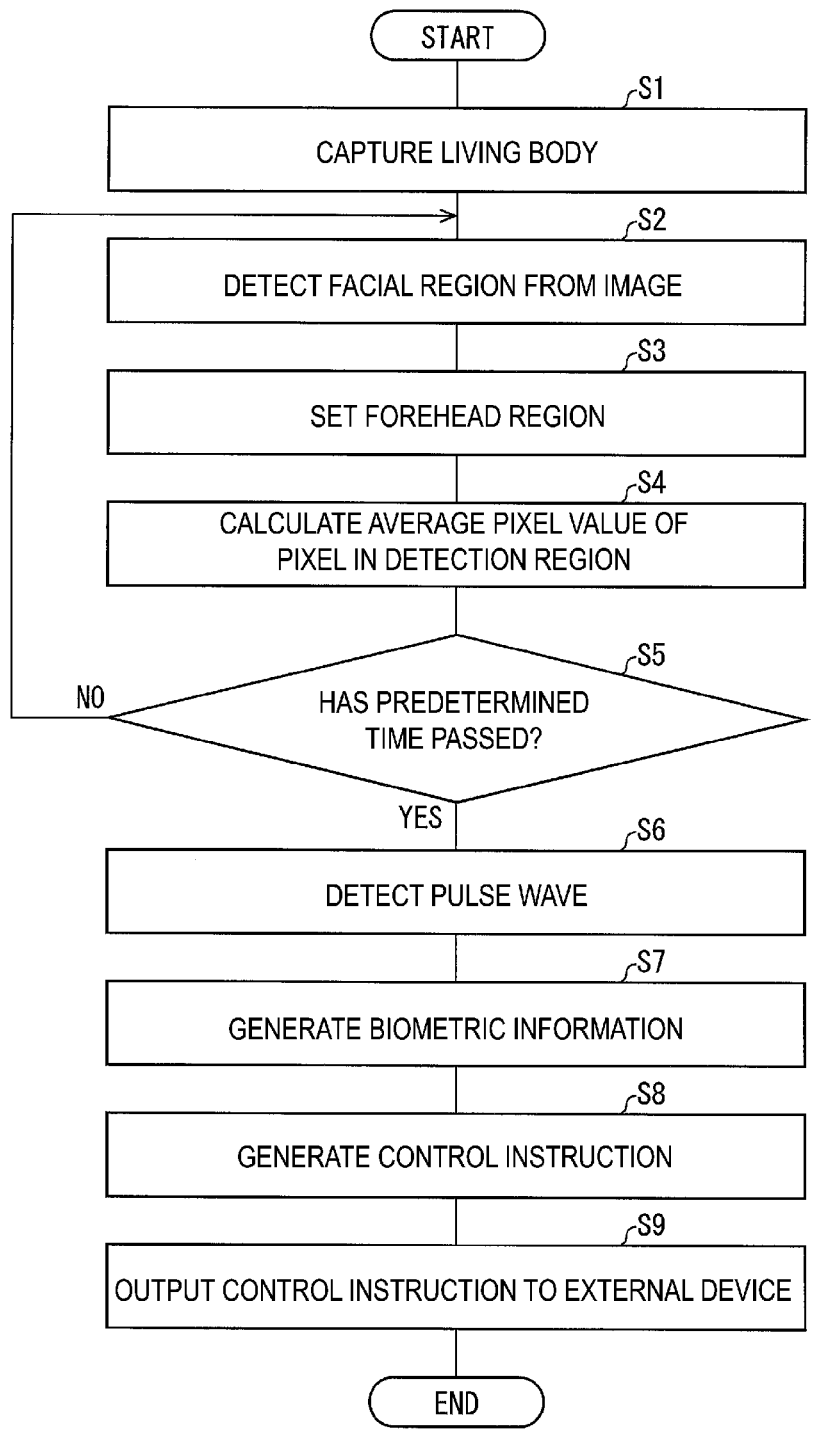
FIG. 6 is a flowchart illustrating an example of a flow of a process in the biometric information generation system.

Next, operations of the biometric information generation system 1A will be described with reference to FIG. 6. FIG. 6 is a flowchart illustrating an example of a flow of a process in the biometric information generation system 1A.

As illustrated in FIG. 6, the biometric information generation system 1A first captures an image of a living body with the camera 10A (S1), and outputs the captured moving picture of the living body to the image analysis unit 20A.

Next, the detection region setting unit 21A detects the facial region F of the living body in the moving picture of the living body outputted from the camera 10A (S2).

Next, the detection region setting unit 21A sets the forehead region D in the detected facial region F of the living body (S3).

Next, the pixel value calculation unit 22A calculates an average pixel value of each color in the forehead region D using the light intensity (pixel value) of each color for each pixel indicated by the moving picture outputted from the camera 10A (S4).

Next, the pixel value calculation unit 22A determines whether the average pixel value has been calculated for a predetermined amount of time (S5). In a case that the average pixel value has not been calculated for the predetermined amount of time (NO in S5), the process returns to step S2. On the other hand, in a case that the average pixel value has been calculated for the predetermined amount of time (YES in S5), the pixel value calculation unit 22A outputs the calculated average pixel value of each color to the pulse wave detection unit 23A.

Next, the pulse wave detection unit 23A detects pulse waves from the average pixel value of each color calculated by the pixel value calculation unit 22A (S6), and outputs the detected pulse waves to the biometric information generation device 3A.

Next, the stress level calculation unit 31, the heart rate calculation unit 32, and the blood pressure calculation unit 33A generate biometric information on the basis of the pulse waves outputted from the pulse wave detection unit 23A (image analysis unit 20A) (S7) and output the generated biometric information to the control instruction generation unit 34A.

Subsequently, the control instruction generation unit 34A generates a control instruction for the external device 90 on the basis of the biometric information outputted from the stress level calculation unit 31, the heart rate calculation unit 32, and the blood pressure calculation unit 33A (S8) and outputs the control instruction to the external device 90 (S9).

As described above, the pulse wave detection device 2A according to the present embodiment includes the camera 10A configured to capture an image of a living body a plurality of times through the first green filter 12 or the infrared light filter 14 having light transmission characteristics in a near-infrared light wavelength range within a wavelength range where the light absorption coefficient of oxidized hemoglobin is greater than the light absorption coefficient of reduced hemoglobin and the image analysis unit 20A configured to detect the pulse waves of the living body by analyzing the plurality of images of the living body captured by the camera 10A. Then, the image analysis unit 20A detects the pulse waves by detecting a change in the intensity of light in the near-infrared light wavelength range indicated by the plurality of images.

According to the configuration described above, the image analysis unit 20A detects the change in the intensity of light in the near-infrared light wavelength range indicated by the plurality of images of the living body captured by the camera 10A through the first green filter 12 or the infrared light filter 14. Since a transmitting depth of the near-infrared light inside the living body is deep, the plurality of images of the living body captured by the camera 10A include information on blood vessels deep in the living body such as an arteriole that contracts and relaxes in accordance with the autonomic nerve of the living body so that the volume flow of blood therein changes. Accordingly, the pulse wave detection device 2A configured to detect pulse waves of the living body by detecting a change in the intensity of light in the near-infrared light wavelength range indicated by the plurality of images of the living body captured by the camera 10A, is capable of detecting the pulse waves of the living body with high accuracy as compared with the existing pulse wave detection devices configured to detect pulse waves by detecting a change in the intensity of light in the visible light wavelength range.

In addition, because the near-infrared light is unlikely to be affected by various ambient light environments, external disturbance such as make-ups of the face of the living body, and the like at the time of measurement, the pulse wave detection device 2A can detect the pulse waves of the living body with higher accuracy.

The biometric information generation system 1A is provided with the pulse wave detection device 2A and the biometric information generation device 3A configured to generate the biometric information on the living body on the basis of the pulse waves of the living body detected by the pulse wave detection device 2A.

According to the configuration described above, the biometric information generation device 3A generates the biometric information on the living body using the pulse waves detected with high accuracy by the pulse wave detection device 2A. In this way, the biometric information generation system 1A can more accurately generate the biometric information on the living body.

The biometric information generation system 1A includes the control instruction generation unit configured to generate a control instruction for controlling the external device 90 on the basis of the biometric information on the living body generated by the biometric information generation device. In this way, the biometric information generation system 1A can operate the external device 90 in response to a situation of the living body.

In addition, by recording data regarding a user such as height, weight, and age in the biometric information generation system 1A in advance, the biometric information can be more accurately calculated.

In a case where the blood pressure measured with a cuff type blood manometer and the blood pressure calculated by the biometric information generation system 1A are measured at the same time, and a correction coefficient calculated from the measured two blood pressures is recorded in the biometric information generation system 1A in advance, the blood pressure can be more accurately calculated by correcting, with the correction coefficient, the blood pressure calculated by the biometric information generation system 1A.

Modification 1

Next, a biometric information generation system 1B as a modification of the biometric information generation system 1A will be described. Note that, for convenience of description, components having the same function as that of components described in the above embodiment are designated by the same reference numerals, and the descriptions of these components will be omitted.

Configuration of Biological Information Generation System 1B

Figure 7:
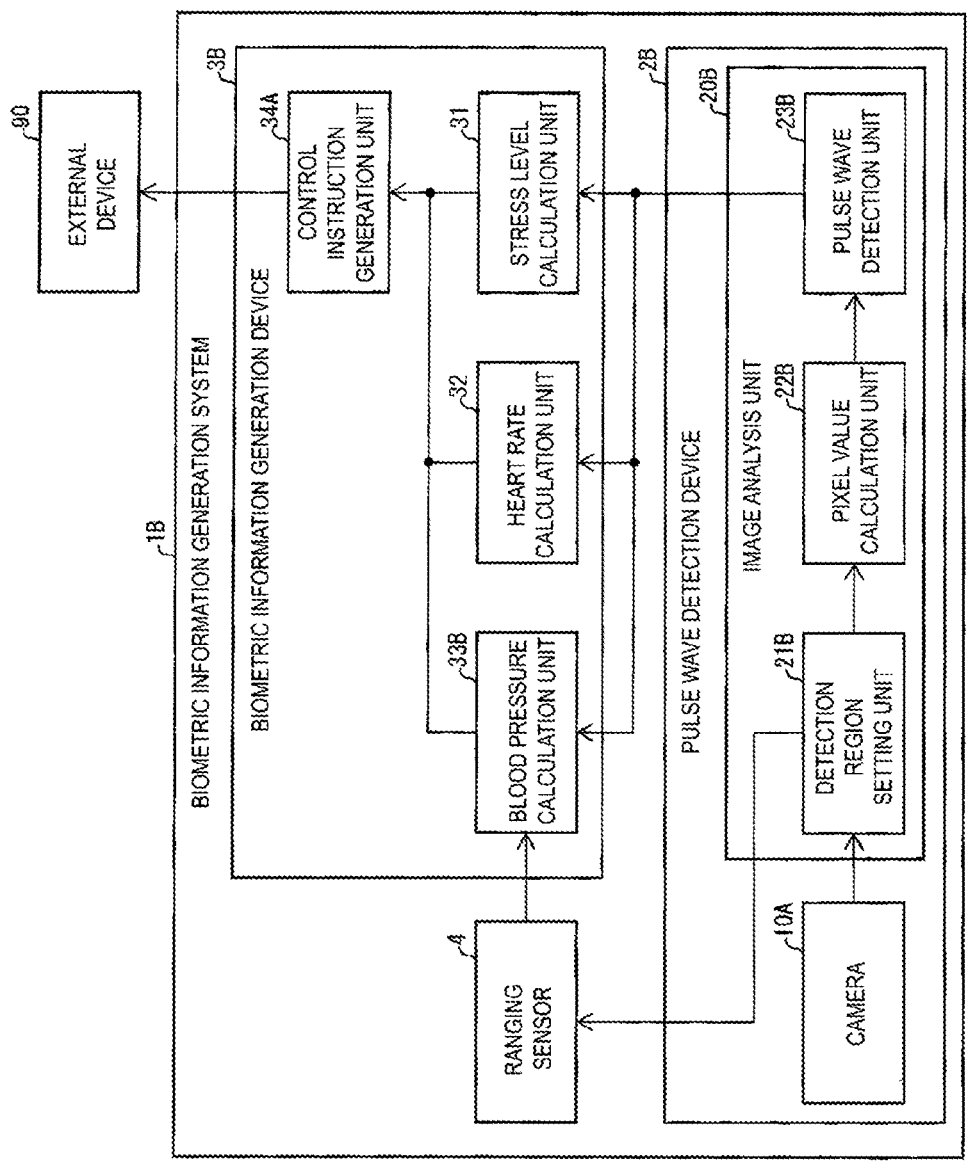
FIG. 7 is a block diagram illustrating a configuration of a main portion of a biometric information generation system as a modification of the above-mentioned biometric information generation system.

The configuration of the biometric information generation system 1B will be described with reference to FIG. 7. FIG. 7 is a block diagram illustrating the configuration of a main portion of the biometric information generation system 1B.

As illustrated in FIG. 7, the biometric information generation system 1B includes a pulse wave detection device 2B and a biometric information generation device 3B in place of the pulse wave detection device 2A and the biometric information generation device 3A in the biometric information generation system 1A. In addition to the configuration of the biometric information generation system 1A, the biometric information generation system 1B includes a ranging sensor 4.

The pulse wave detection device 2B includes an image analysis unit 20B in place of the image analysis unit 20A in the pulse wave detection device 2A of the biometric information generation system 1A. The image analysis unit 20B includes a detection region setting unit 21B, a pixel value calculation unit 22B, and a pulse wave detection unit 23B in place of the detection region setting unit 21A, the pixel value calculation unit 22A, and the pulse wave detection unit 23A in the image analysis unit 20A.

The detection region setting unit 21B sets two detection regions for detecting pulse waves in each of captured images constituting a moving picture of a living body outputted from a camera 10A. For example, the detection region setting unit 21B may set the forehead and the nose as the detection regions. The setting of the detection regions may be performed by a method similar to that in the detection region setting unit 21A.

The pixel value calculation unit 22B calculates an average pixel value of each color in each of the two detection regions set by the detection region setting unit 21B. The calculation of the average pixel value may be performed by a method similar to that in the pixel value calculation unit 22A.

The pulse wave detection unit 23B calculates respective pulse waves from the average pixel values at the two detection regions calculated by the pixel value calculation unit 22B. The calculation of the pulse waves can be performed by a method similar to that in the pulse wave detection unit 23A.

The ranging sensor 4 measures a distance between the two detection regions set in the detection region setting unit 21B (i.e., detects the distance between the two detection regions). The ranging sensor 4 according to the present modification is a triangulation type ranging sensor configured to calculate a distance on the basis of a change in imaging position of the light receiving element due to the distance change, but is not limited thereto. The ranging sensor may be, for example, a time-of-flight type ranging sensor in which a time from when light is emitted from the ranging sensor to when the light is received is measured, and then the distance is calculated on the basis of the measured time. The ranging sensor 4 outputs the measured distance between the two detection regions to the blood pressure calculation unit 33B.

The biometric information generation device 3B includes a blood pressure calculation unit 33B in place of the blood pressure calculation unit 33A in the biometric information generation device 3A of the biometric information generation system 1A.

The blood pressure calculation unit 33B calculates blood pressure of the living body on the basis of the pulse waves at the two detection regions outputted from the pulse wave detection device 2B and the distance between the two detection regions measured by the ranging sensor 4.

Specifically, the blood pressure calculation unit 33B first calculates a pulse wave velocity using the pulse waves at the two detection regions outputted from the pulse wave detection device 2B. More specifically, the blood pressure calculation unit 33B calculates the pulse wave velocity by dividing the distance between the two detection regions measured by the ranging sensor 4 by a time difference between the pulse wave rise times at the two detection regions.

As described above, the pulse wave velocity and the blood pressure are correlated with each other. Thus, in advance, data of the pulse wave velocity and data of the blood pressure are acquired, and then a calculation formula for the blood pressure is created by performing, for example, a multiple regression analysis using these data. Then, the blood pressure calculation unit 33B calculates the blood pressure of the living body by giving the pulse wave velocity to the above-mentioned calculation formula.

As described above, since the biometric information generation system 1B includes the ranging sensor 4 and calculates the blood pressure of the living body (generates the biometric information) on the basis of the distance between the two detection regions detected by the ranging sensor 4 and the pulse waves detected by the pulse wave detection device 2B, the blood pressure of the living body can be more accurately calculated.

In addition, for example, the blood pressure of a living body can be measured by mounting the biometric information generation system according to an aspect of the present disclosure in a smartphone and calculating the pulse wave velocity using functions included in the smartphone. Here, it is assumed that the smartphone includes a main camera, a white Light Emitting Diode (LED) provided proximate to the main camera, and an in-camera (sub-camera) for capturing the face of the user. First, by making the user's index finger brought into contact with the main camera and the white LED, the pulse waves are detected from the index finger of the user. At the same time, pulse waves are detected from the user's face by the above-described in-camera. Then, the blood pressure of the living body can also be calculated by detecting the pulse wave velocity on the basis of the pulse waves detected from the user's index finger and the pulse waves detected from the user's face and giving the detected pulse wave velocity to the above-discussed formula.

Modification 2

Next, a biometric information generation system 1C as another modification of the biometric information generation system 1A will be described. Note that, for convenience of description, components having the same function as that of components described in the above embodiment are designated by the same reference numerals, and the descriptions of these components will be omitted.

Configuration of Biometric Information Generation System 1C

Figure 8:
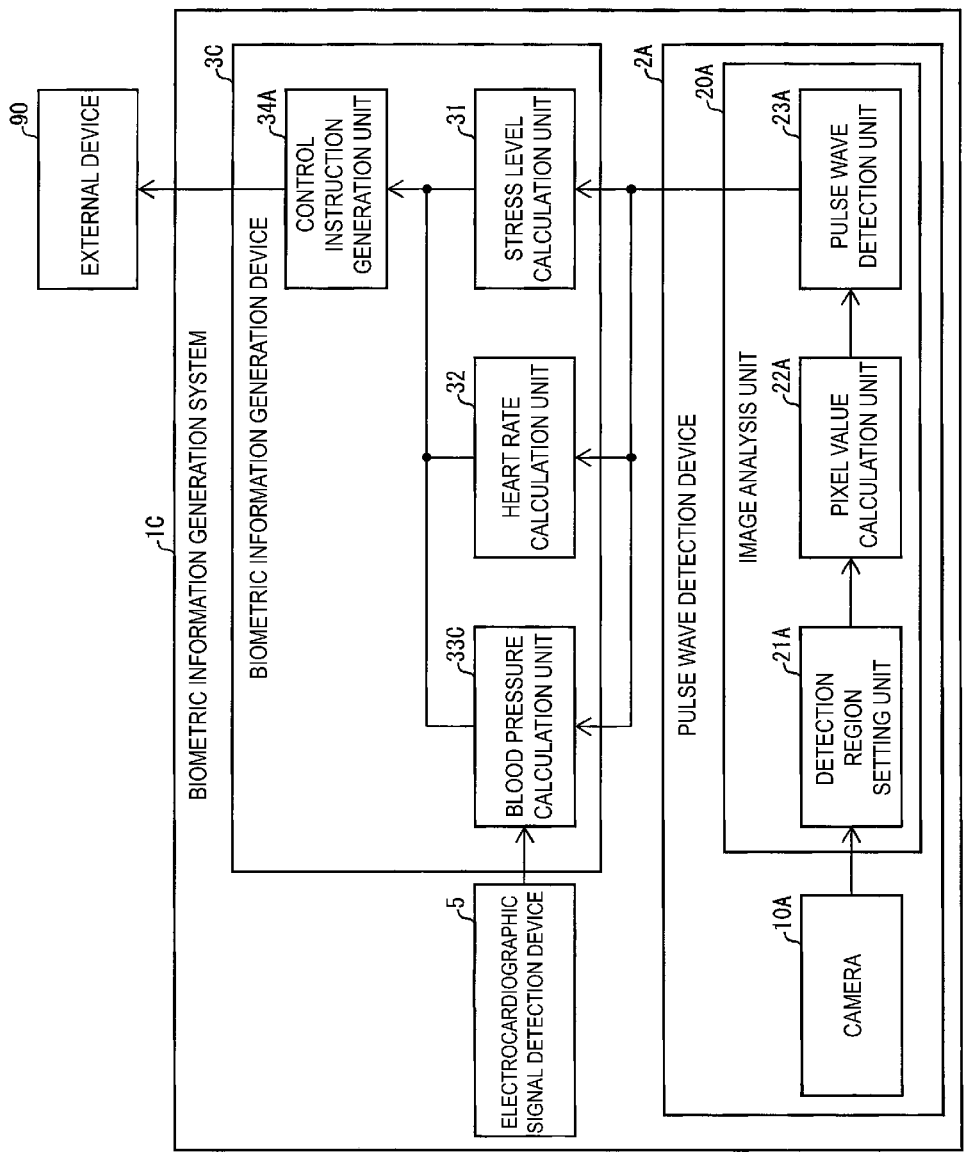
FIG. 8 is a block diagram illustrating a configuration of a main portion of a biometric information generation system as another modification of the above-mentioned biometric information generation system.

The configuration of the biometric information generation system 1C will be described with reference to FIG. 8. FIG. 8 is a block diagram illustrating the configuration of a main portion of the biometric information generation system 1C.

As illustrated in FIG. 8, the biometric information generation system 1C includes a biometric information generation device 3C in place of the biometric information generation device 3A in the biometric information generation system 1A. In addition to the configuration of the biometric information generation system 1A, the biometric information generation system 1C includes an electrocardiographic signal detection device 5.

The electrocardiographic signal detection device 5 is an electrocardiograph configured to detect an electrocardiographic signal of a living body. The electrocardiographic signal detection device 5 outputs the detected electrocardiographic signal of the living body to a blood pressure calculation unit 33C, which will be described later.

The biometric information generation device 3C includes the blood pressure calculation unit 33C in place of the blood pressure calculation unit 33A in the biometric information generation device 3A of the biometric information generation system 1A.

The blood pressure calculation unit 33C calculates the blood pressure of the living body on the basis of the pulse waves outputted from a pulse wave detection device 2A and the electrocardiographic signal of the living body detected by the electrocardiographic signal detection device 5.

Specifically, the blood pressure calculation unit 33C first calculates a pulse wave propagation time from a time difference between the time of a peak (or rise of a peak) in the electrocardiographic signal detected by the electrocardiographic signal detection device 5 and the time of a peak (or rise of a peak) in the pulse waves outputted from the pulse wave detection device 2A. Here, there is a correlation between the pulse wave propagation time and the blood pressure. Thus, in advance, data of the pulse wave propagation time and data of the blood pressure are acquired, and then a calculation formula for the blood pressure is created by performing, for example, a multiple regression analysis using these data. Then, the blood pressure calculation unit 33C calculates the blood pressure of the living body by giving the calculated pulse wave propagation time to the above-mentioned calculation formula.

As described above, since the biometric information generation system 1C includes the electrocardiographic signal detection device 5 and calculates the blood pressure of the living body (generates the biometric information) on the basis of the electrocardiographic signal detected by the electrocardiographic signal detection device 5 and the pulse waves detected by the pulse wave detection device 2A, the blood pressure of the living body can be more accurately calculated.

Note that, the blood pressure calculation unit 33B in the biometric information generation system 1B determines a pulse wave propagation time from a time difference between the rise times of the pulse waves detected at the two detection regions outputted from the pulse wave detection device 2B and can calculate the blood pressure of the living body similarly to the blood pressure calculation unit 33C in the biometric information generation system 1C (i.e., similar to the case where the pulse wave propagation time is calculated from electrocardiographic signal).

Modification 3

Next, a biometric information generation system 1D as another modification of the biometric information generation system 1A will be described. Note that, for convenience of description, components having the same function as that of components described in the above embodiment are designated by the same reference numerals, and the descriptions of these components will be omitted.

Figure 9:
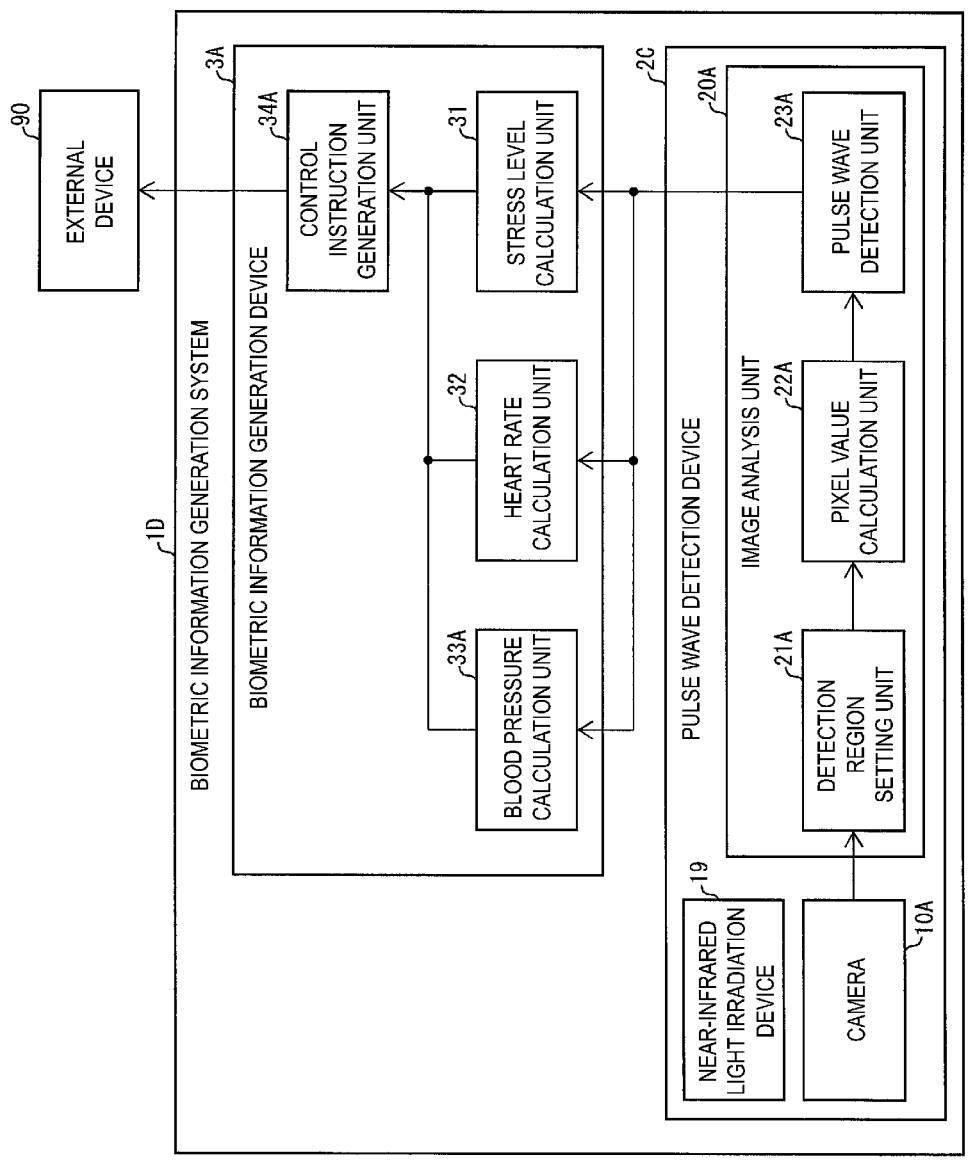
FIG. 9 is a block diagram illustrating a configuration of a main portion of a biometric information generation system as still another modification of the above-mentioned biometric information generation system.

The configuration of the biometric information generation system 1D will be described with reference to FIG. 9. FIG. 9 is a block diagram illustrating the configuration of a main portion of the biometric information generation system 1D.

As illustrated in FIG. 9, the biometric information generation system 1D includes a pulse wave detection device 2C in place of the pulse wave detection device 2A in the biometric information generation system 1A.

In addition to the configuration of the pulse wave detection device 2A in the biometric information generation system 1A, the pulse wave detection device 2C further includes a near-infrared light irradiation device 19.

The near-infrared light irradiation device 19 is an irradiation device configured to emit near-infrared light and irradiates the living body with the near-infrared light in a case that the camera 10A captures a moving picture of the living body.

As described above, the pulse wave detection device 2C includes the near-infrared light irradiation device 19. As a result, reflected light of the near-infrared light allowed to be transmitted deep in the living body can be detected more strongly by the camera 10A, and therefore the pulse waves of the living body can be detected with higher accuracy in an image analysis unit 20A.

Second Embodiment

Another embodiment of the present disclosure will be described below with reference to FIGS. 10 to 12. Note that, for convenience of description, components having the same function as that of components described in the above embodiment are designated by the same reference numerals, and the descriptions of these components will be omitted.

The configuration of a camera 10B of a biometric information generation system 1E of the present embodiment differs from the configuration of the camera 10A of the biometric information generation system 1A of the first embodiment.

Configuration of Biometric Information Generation System 1E

The configuration of the biometric information generation system 1E will be described with reference to FIG. 10. FIG. 10 is a block diagram illustrating the configuration of a main portion of the biometric information generation system 1E.

Figure 10:
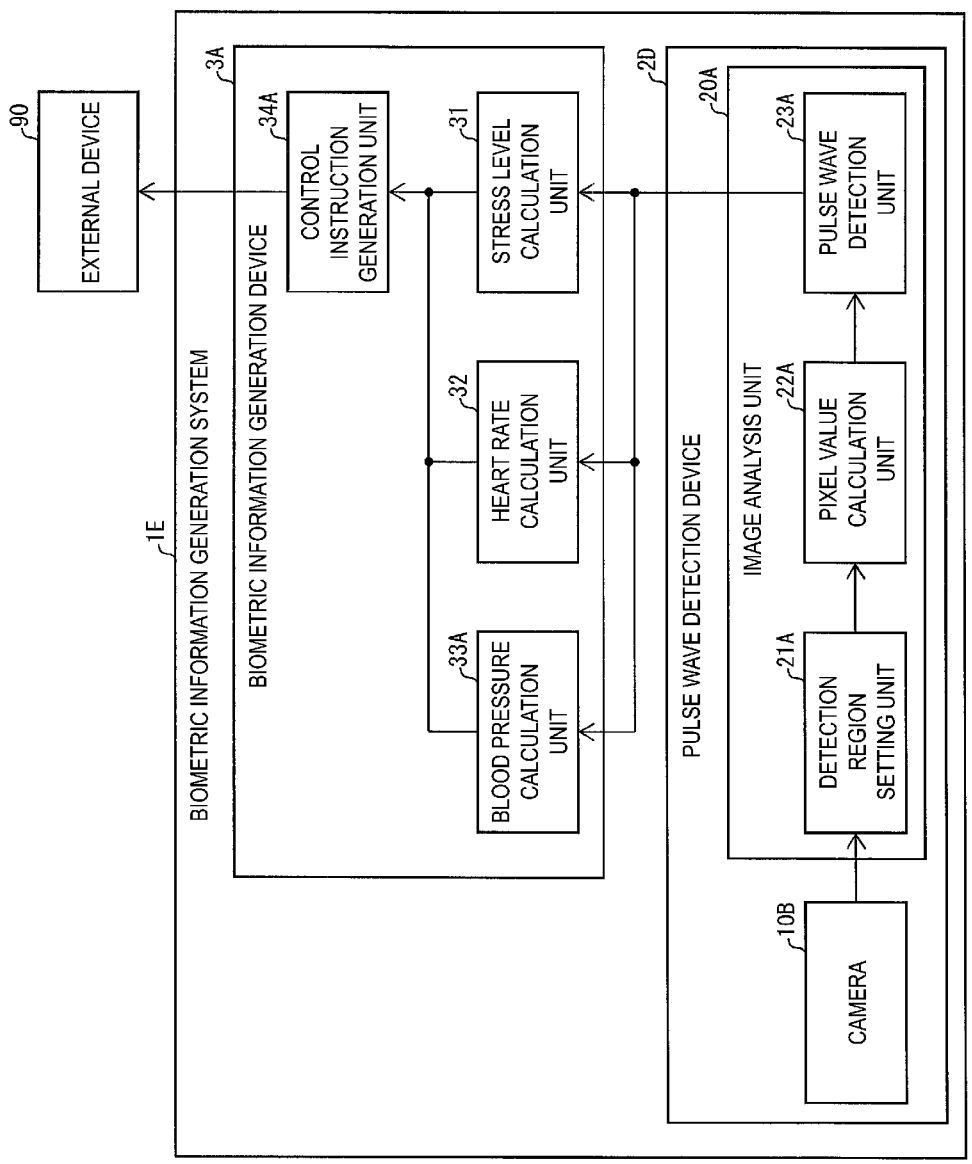
FIG. 10 is a block diagram illustrating a configuration of a main portion of a biometric information generation system according to a second embodiment of the present disclosure.

As illustrated in FIG. 10, the biometric information generation system 1E includes a pulse wave detection device 2D in place of the pulse wave detection device 2A in the biometric information generation system 1A.

The pulse wave detection device 2D includes the camera 10B in place of the camera 10A in the pulse wave detection device 2A of the biometric information generation system 1A. The camera 10B will be described with reference to FIG. 11. FIG. 11 is a schematic diagram illustrating the configuration of the camera 10B.

Figure 11:
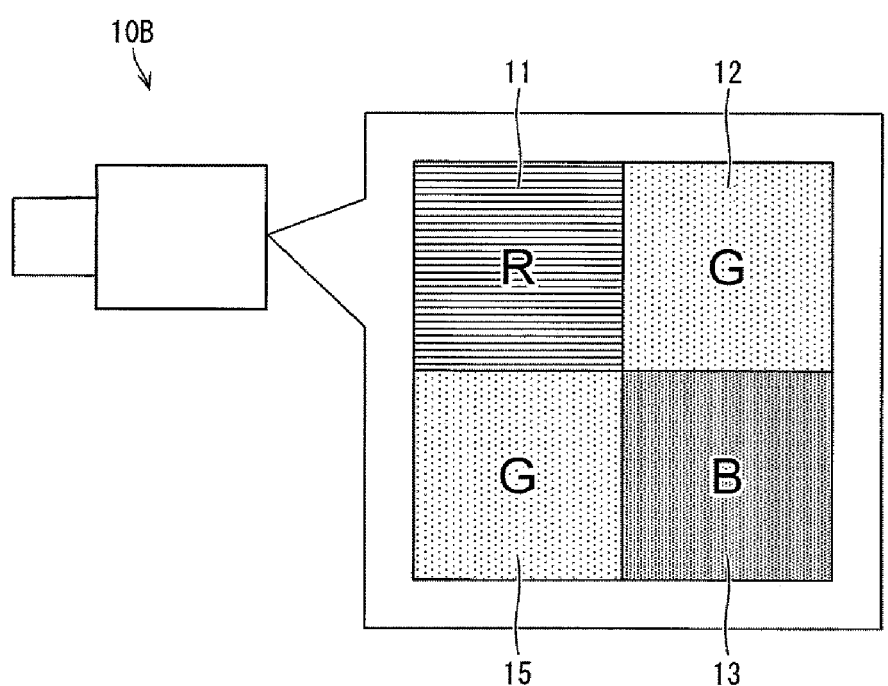
FIG. 11 is a schematic diagram illustrating a configuration of a camera included in the biometric information generation system.
Figure 12:
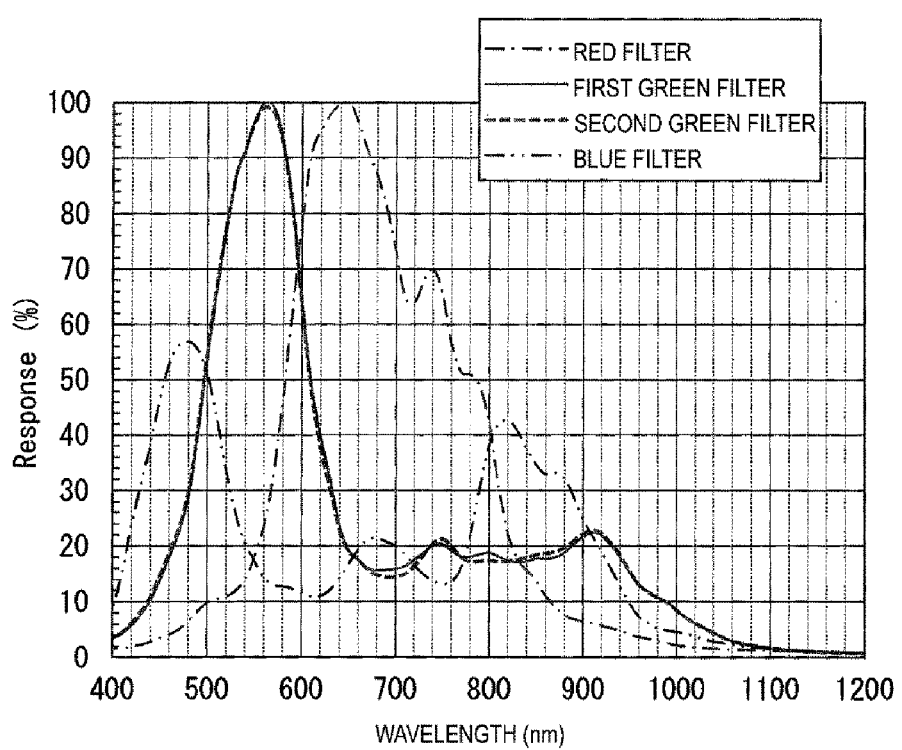
FIG. 12 is a graph showing light transmittance of a red filter, a first green filter, a blue filter, and a second green filter included in the camera.

As illustrated in FIG. 11, in the camera 10B, any of a red filter 11, a first green filter 12, a blue filter 13, and a second green filter (second filter) 15 is provided in each of a plurality of light receiving elements included in an image sensor (not illustrated). The camera 10B detects intensity (luminance) of light having passed through each of the red filter 11, the first green filter 12, the blue filter 13, and the second green filter 15 and generates a captured image. Each pixel in the captured image is formed by the light receiving element provided with any of the four types of filters described above.

Transmission characteristics (sensitivity characteristics) of the second green filter 15 will be described with reference to FIG. 12. FIG. 12 is a graph showing light transmittance of the second green filter 15. In FIG. 12, light transmittance of each of the red filter 11, the first green filter 12, and the blue filter 13 are also shown together. As shown in FIG. 12, the second green filter 15, like the first green filter 12, transmits the light of a wavelength from about 500 nm to about 600 nm in a green visible light wavelength range and the light of a wavelength equal to or longer than about 805 nm in the near-infrared range.

The camera 10B generates a moving picture in which an imaging target subject (living body) is captured, based on the intensity of the light having passed through the red filter 11, the intensity of the light having passed through the first green filter 12, and the intensity of the light having passed through the blue filter 13 and the second green filter 15, and then outputs the generated moving picture to an image analysis unit 20A.

An image processing method for detecting a pulse wave in the image analysis unit 20A is similar to that of the first embodiment, and thus description thereof will be omitted.

As described above, the pulse wave detection device 2D in the present embodiment detects pulse waves of a living body using images captured through the second green filter 15 having light transmission characteristics in the green wavelength range along with images captured through the first green filter 12. As described above, the green wavelength range includes a wavelength region from 529 to 546 nm and a wavelength range from 569 to 584 nm, in which the light absorption coefficient of oxidized hemoglobin is greater than the light absorption coefficient of reduced hemoglobin. Accordingly, because the pulse wave detection device 2D detects the pulse waves of the living body using the images captured through the second green filter 15 having light transmission characteristics in the green wavelength range along with the images captured through the first green filter 12, a larger amount of blood vessel information on the living body can be detected so that the pulse waves of the living body can be detected with high accuracy.

Third Embodiment

Another embodiment of the present disclosure will be described below with reference to FIGS. 13 to 15.

The configuration of a camera 10C of a biometric information generation system 1F of the present embodiment differs from the configuration of the camera 10A of the biometric information generation system 1A of the first embodiment.

Configuration of Biometric Information Generation System 1F

The configuration of the biometric information generation system 1F will be described with reference to FIG. 13. FIG. 13 is a block diagram illustrating the configuration of a main portion of the biometric information generation system 1F.

Figure 13:
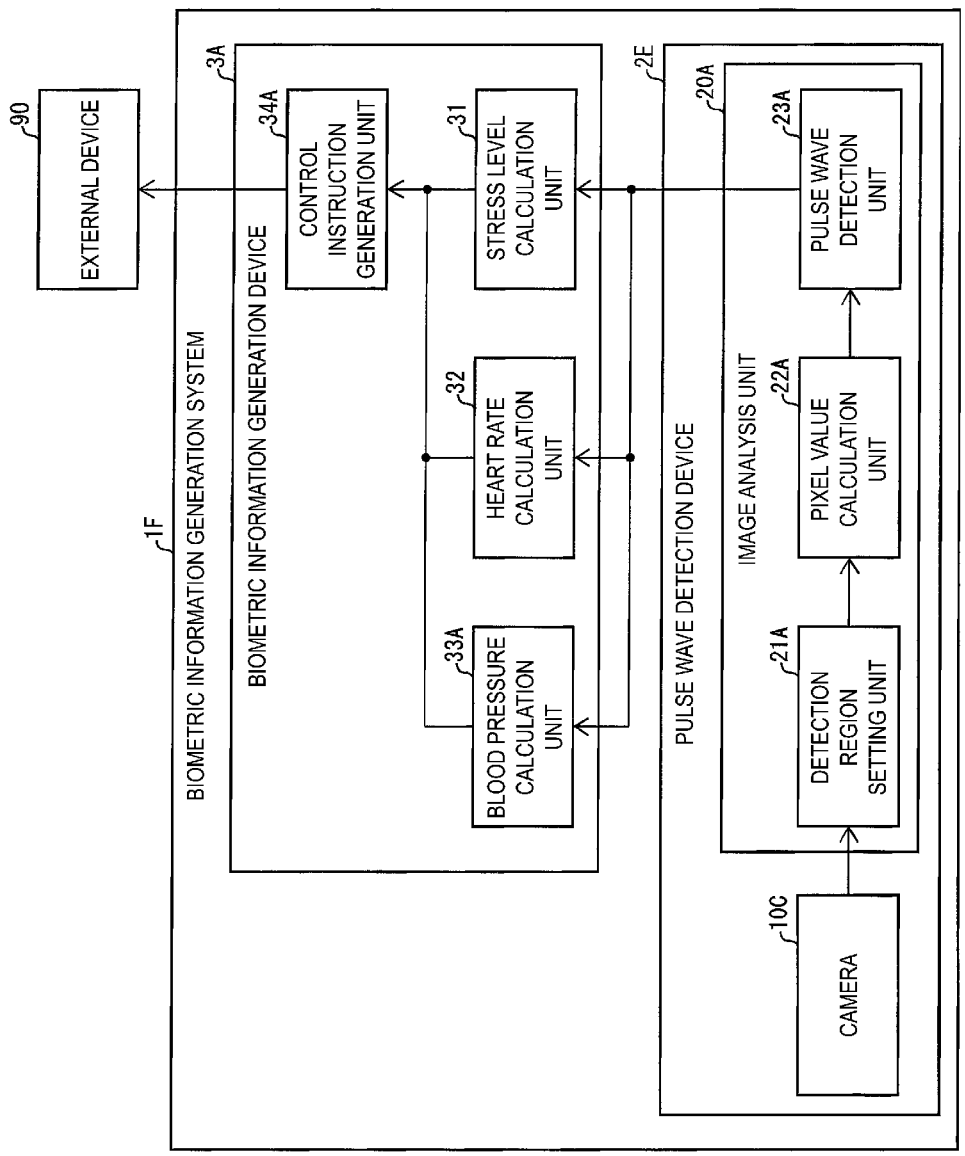
FIG. 13 is a block diagram illustrating a configuration of a main portion of a biometric information generation system according to a third embodiment of the present disclosure.

As illustrated in FIG. 13, the biometric information generation system 1F includes a pulse wave detection device 2E in place of the pulse wave detection device 2A in the biometric information generation system 1A.

The pulse wave detection device 2E includes the camera 10C in place of the camera 10A in the pulse wave detection device 2A of the biometric information generation system 1A. The camera 10C will be described with reference to FIG. 14. FIG. 14 is a schematic diagram illustrating the configuration of the camera 10C.

Figure 14:
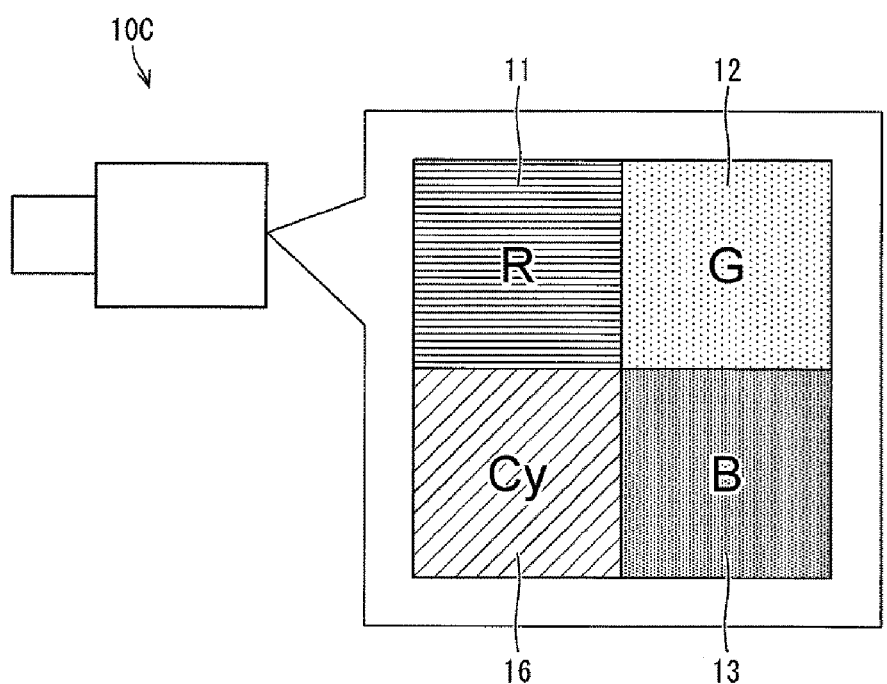
FIG. 14 is a schematic diagram illustrating a configuration of a camera included in the biometric information generation system.
Figure 15:
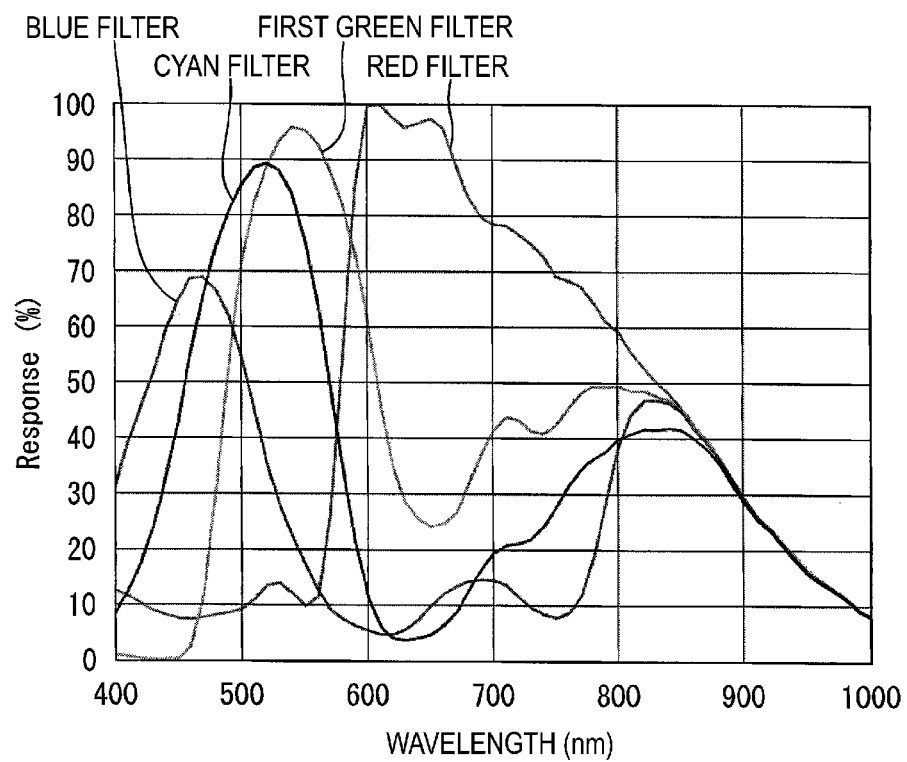
FIG. 15 is a graph showing light transmittance of a red filter, a first green filter, a blue filter, and a cyan filter included in the camera.

As illustrated in FIG. 14, in the camera 10C, any of a red filter 11, a first green filter 12, a blue filter 13, and a cyan filter (second filter) 16 is provided in each of a plurality of light receiving elements included in an image sensor (not illustrated). The camera 10C detects intensity (luminance) of light having passed through each of the red filter 11, the first green filter 12, the blue filter 13 and the cyan filter 16 and generates a captured image. Each pixel in the captured image is formed by the light receiving element provided with any of the four types of filters described above.

Transmission characteristics (sensitivity characteristics) of the cyan filter 16 will be described with reference to FIG. 15. FIG. 15 is a graph showing light transmittance of the cyan filter 16. In FIG. 15, light transmittance of the red filter 11, the first green filter 12, and the blue filter 13 are also shown together. As shown in FIG. 15, the cyan filter 16 transmits the light of a wavelength from about 450 nm to about 550 nm in a green visible light wavelength range and the light of a wavelength equal to or longer than about 805 nm in the near-infrared range.

The camera 10C generates a moving picture in which an imaging target subject (living body) is captured, based on the intensity of the light having passed through the red filter 11, the intensity of the light having passed through the first green filter 12, and the intensity of the light having passed through the blue filter 13 and the cyan filter 16 and then outputs the generated moving picture to an image analysis unit 20A.

As described above, the pulse wave detection device 2E in the present embodiment detects pulse waves of a living body using images captured through the cyan filter 16 having light transmission characteristics in the cyan wavelength range along with images captured through the first green filter 12. Here, the cyan wavelength range includes a wavelength region from 453 to 499 nm and a wavelength range from 529 to 546 nm, in which the light absorption coefficient of oxidized hemoglobin is greater than the light absorption coefficient of reduced hemoglobin. Accordingly, because the pulse wave detection device 2E detects the pulse waves of the living body using the images captured through the cyan filter 16 having light transmission characteristics in the cyan wavelength range along with the images captured through the first green filter 12, a larger amount of blood vessel information on the living body can be detected so that the pulse waves of the living body can be detected with high accuracy.

Fourth Embodiment

Another embodiment of the present disclosure will be described as follows with reference to FIG. 16 and FIG. 17.

Pulse waves of a living body change in accordance with motion of the living body. As such, a biometric information generation system 1G according to the present embodiment differs from the biometric information generation system 1A in a point that a motion sensor 6 is included, and pulse waves are corrected and a control instruction for an external device 90 is generated on the basis of the motion of the living body detected by the motion sensor 6.

Configuration of Biometric Information Generation System 1G

The configuration of the biometric information generation system 1G will be described with reference to FIG. 16. FIG. 16 is a block diagram illustrating the configuration of a main portion of the biometric information generation system 1G.

Figure 16:
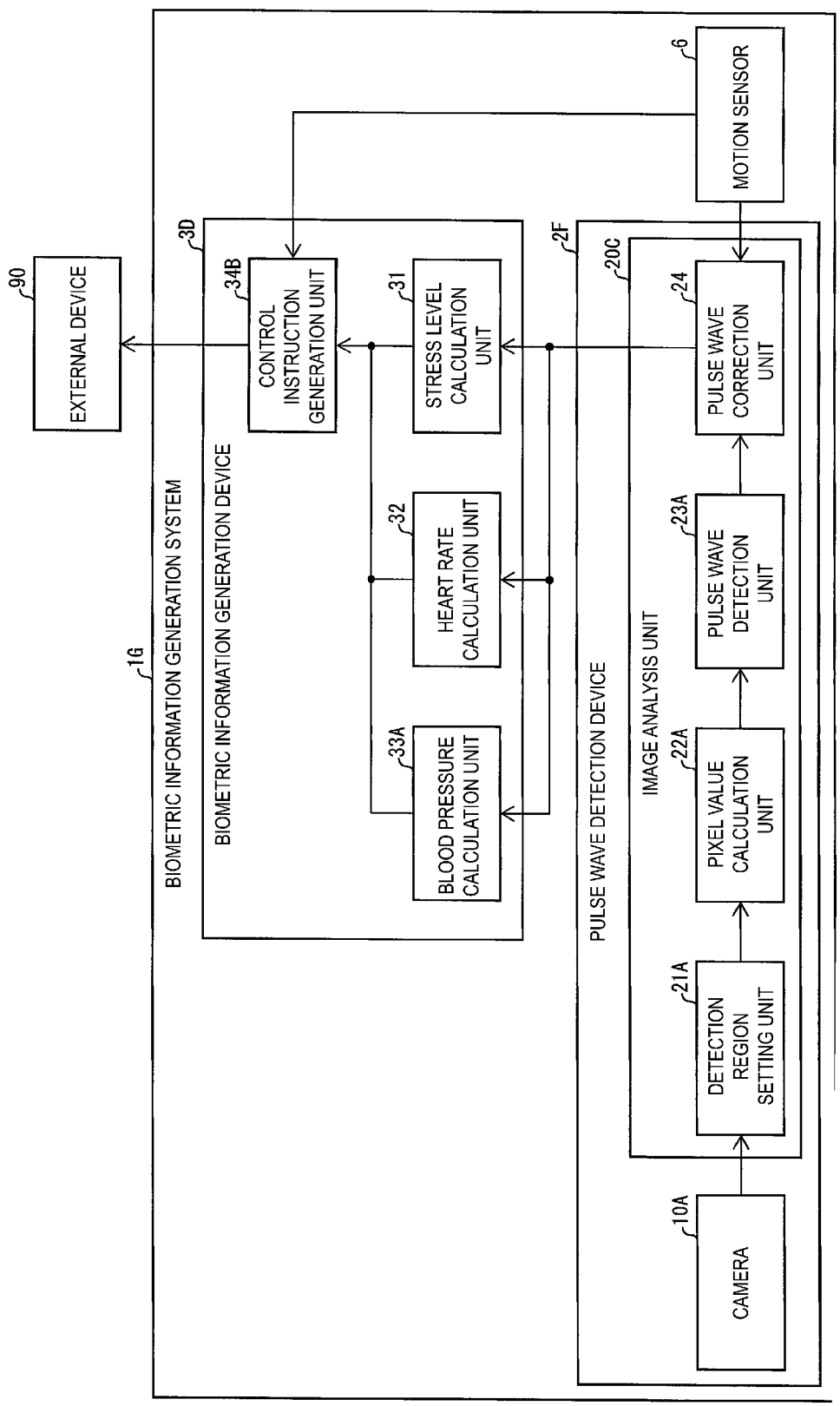
FIG. 16 is a block diagram illustrating a configuration of a main portion of a biometric information generation system according to a fourth embodiment of the present disclosure.

As illustrated in FIG. 16, the biometric information generation system 1G includes a pulse wave detection device 2F and a biometric information generation device 3D in place of the pulse wave detection device 2A and the biometric information generation device 3A in the biometric information generation system 1A. The biometric information generation system 1G also includes the motion sensor (gesture sensor) 6 in addition to the configuration of the biometric information generation system 1A.

The motion sensor 6 is a sensor configured to detect motion (gesture) of a living body. The motion sensor 6 includes an illuminator (not illustrated) configured to emit near-infrared light, a camera (not illustrated) configured to detect the near-infrared light emitted from the illuminator and reflected at the living body, and a detector (not illustrated) configured to detect the motion of the living body on the basis of a change in the intensity of the near-infrared light detected by the camera. The motion sensor 6 outputs information indicating the detected motion of the living body to a pulse wave correction unit 24 and a control instruction generation unit 34B, which will be described later.

The pulse wave detection device 2F includes an image analysis unit 20C in place of the image analysis unit 20A in the pulse wave detection device 2A of the biometric information generation system 1A. In addition to the configuration of the image analysis unit 20A, the image analysis unit 20C includes the pulse wave correction unit (correction unit) 24.

The pulse wave correction unit 24 corrects pulse waves detected by a pulse wave detection unit 23A on the basis of the motion of the living body detected by the motion sensor 6.

For example, in a case where the face of the living body moves in a vertical direction due to motion such as vertical movement of the head or tilting of the body, the pulse waves are changed because the pressure applied to the blood vessel of the living body changes. Then, the pulse wave correction unit 24 presets a correction amount of pulse waves associated with a specific motion of the living body, corrects the pulse waves detected by the pulse wave detection unit 23A with the above-mentioned correction amount on the basis of the motion of the living body detected by the motion sensor 6, and then outputs the corrected pulse waves to the biometric information generation device 3D. This allows the pulse wave detection device 2F to detect the pulse waves of the living body with higher accuracy.

Note that, for example, in a case where the motion of the body of the living body is larger than a predetermined degree of motion, such as both hands being moved wildly or the body being rocked left and right, the pulse waves become irregular. Accordingly, it is meaningless to detect the pulse waves during the above-described period. Thus, in the case where the motion of the living body detected by the motion sensor 6 is larger than the predetermined degree of motion, the pulse wave correction unit 24 does not output the pulse waves detected by the pulse wave detection unit 23A to the biometric information generation device 3D. This may suppress a situation in which a detection error of the pulse waves detected by the pulse wave detection device 2F becomes large.

The biometric information generation device 3D includes the control instruction generation unit 34B in place of the control instruction generation unit 34A in the biometric information generation device 3A of the biometric information generation system 1A.

The control instruction generation unit 34B generates a control instruction for an external device 90 on the basis of the motion of the living body detected by the motion sensor 6 and the biometric information outputted from a stress level calculation unit 31, a heart rate calculation unit 32, and a blood pressure calculation unit 33A.

Specifically, in the case where the external device 90 is a robot, the control instruction generation unit 34B issues a control instruction for the robot so that the robot starts to give a speech or gesture in a case that the motion sensor 6 detects the user waving his or her hand to the robot. Furthermore, the control instruction generation unit 34B issues a control instruction for the robot to cause the robot to perform a speech or gesture such that the user can be relaxed in response to the user's biometric information outputted from the stress level calculation unit 31, the heart rate calculation unit 32, and the blood pressure calculation unit 33A. In the case where the external device 90 is a television or a personal computer, the control instruction generation unit 34B issues a control instruction for the television or the personal computer so that the display is widened or reduced in a case that the motion sensor 6 detects the motion of the user extending or narrowing a space between the hands thereof. Furthermore, the control instruction generation unit 34B issues a control instruction for the television or the personal computer to cause the television or the personal computer to output such an image or voice that the user can be relaxed in response to the user's biometric information outputted from the stress level calculation unit 31, the heart rate calculation unit 32, and the blood pressure calculation unit 33A. In the case where the external device 90 is an air-conditioner, the control instruction generation unit 34B issues a control instruction of cooling or heating for the air-conditioner in a case that the motion sensor 6 detects the motion of the user exhibiting that the user feels hot or cold. Furthermore, the control instruction generation unit 34B issues a further detailed control instruction, for the air-conditioner, such as temperature adjustment, an air quantity, or the wind direction in accordance with the user's biometric information outputted from the stress level calculation unit 31, the heart rate calculation unit 32, and the blood pressure calculation unit 33A.

Operations of Biometric Information Generation System 1G

Next, operations of the biometric information generation system 1G will be described with reference to FIG. 17. FIG. 17 is a flowchart illustrating an example of a flow of a process in the biometric information generation system 1G.

Figure 17:
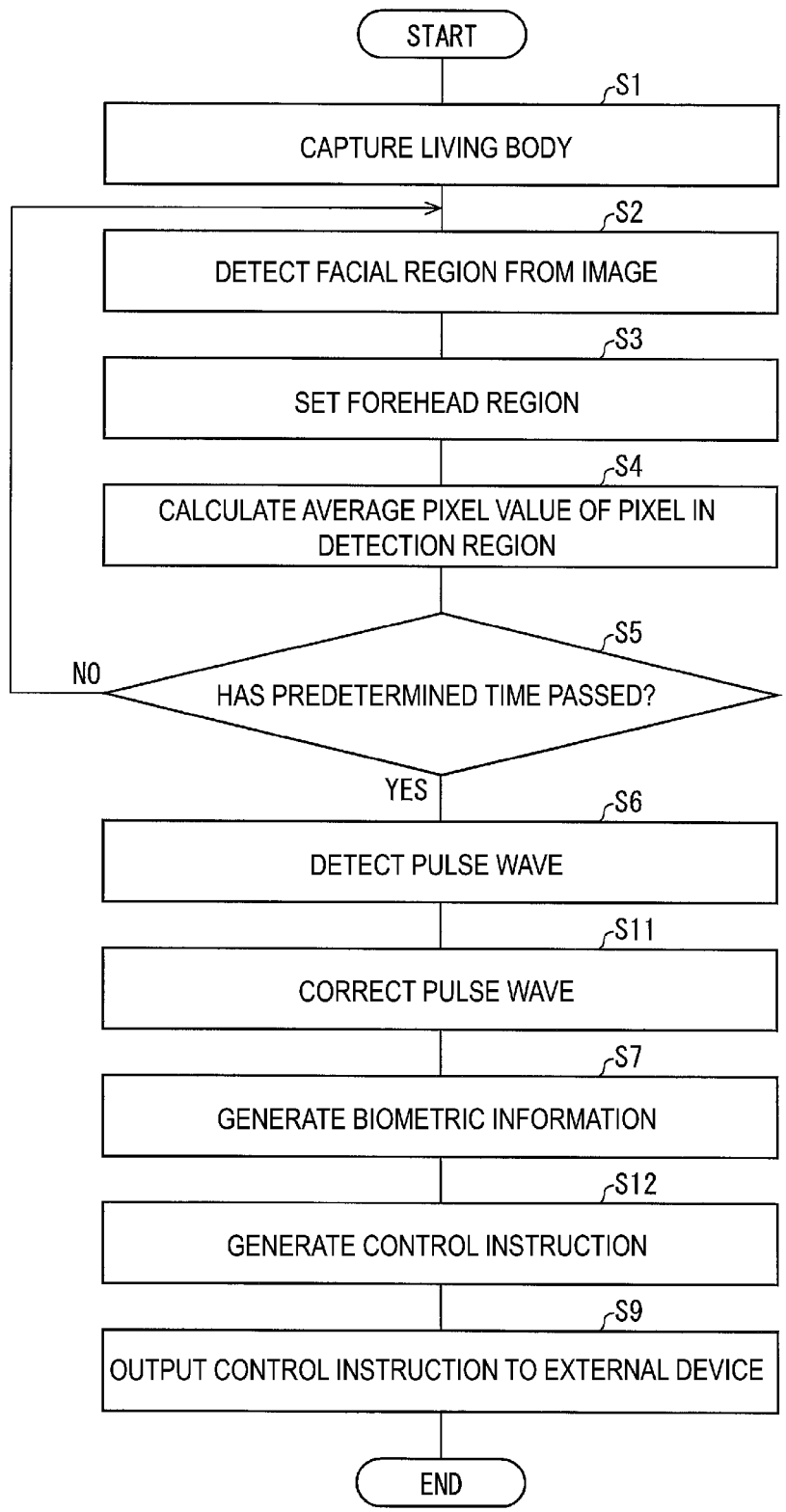
FIG. 17 is a flowchart illustrating an example of a flow of a process in the biometric information generation system.

In the flowchart in FIG. 17, since S1 to S6 are identical to S1 to S6 illustrated in FIG. 6 of the first embodiment, the description thereof is omitted.

In the biometric information generation system 1G, the pulse wave detection unit 23A detects pulse waves (S6); thereafter, the pulse wave correction unit 24 corrects the pulse waves detected by the pulse wave detection unit 23A on the basis of the motion of the living body detected by the motion sensor 6 (S11), and outputs the corrected pulse waves to the biometric information generation device 3D.

Next, the stress level calculation unit 31, the heart rate calculation unit 32, and the blood pressure calculation unit 33A generate biometric information on the basis of the pulse waves outputted from the pulse wave correction unit 24 (image analysis unit 20C) (S7) and output the generated biometric information to the control instruction generation unit 34B (S7).

Subsequently, the control instruction generation unit 34B generates a control instruction for the external device 90 on the basis of the motion of the living body detected by the motion sensor 6 and the biometric information outputted from the stress level calculation unit 31, the heart rate calculation unit 32 and the blood pressure calculation unit 33A (S12) and then outputs the control instruction to the external device 90 (S9).

As described above, the image analysis unit 20C as an image analysis device, includes, as an image analysis unit configured to detect pulse waves of a living body by analyzing images obtained by capturing an image of the living body, a detection region setting unit 21A, a pixel value calculation unit 22A and the pulse wave detection unit 23A, and further includes the pulse wave correction unit 24 configured to correct the pulse waves detected by the detection region setting unit 21A, the pixel value calculation unit 22A, and the pulse wave detection unit 23A on the basis of the motion of the living body detected by the motion sensor 6 configured to detect the motion of the living body. This allows the image analysis unit 20C to detect the pulse waves of the living body with higher accuracy.

The biometric information generation system 1G includes a camera 10A for capturing a living body, the motion sensor 6 configured to detect motion of the living body, the image analysis unit 20C, and the biometric information generation device 3D configured to generate biometric information on the living body on the basis of the pulse waves detected by the image analysis unit 20C. With this, the biometric information generation system 1G can generate biometric information on the living body more accurately on the basis of the detailed pulse waves detected by the image analysis unit 20C.

Furthermore, the biometric information generation system 1G includes the control instruction generation unit configured to generate control instructions for controlling other devices on the basis of the motion of the living body detected by the motion sensor 6 and the biometric information generated by the stress level calculation unit 31, the heart rate calculation unit 32, and the blood pressure calculation unit 33A. With this, the biometric information generation system 1G can generate a control instruction for controlling the external device 90 using both information that appears outside the body of the living body (motion of the living body detected by the motion sensor 6) and information in the body of the living body (biometric information outputted from the stress level calculation unit 31, the heart rate calculation unit 32, and the blood pressure calculation unit 33A). As a result, the biometric information generation system 1G can operate the external device 90 in response to a situation of the living body more appropriately.

Implementation Example by Software

The control blocks of the pulse wave detection devices 2A to 2F (particularly, the image analysis units 20A to 20C) and the control blocks of the biometric information generation devices 3A to 3D (particularly, the stress level calculation unit 31, the heart rate calculation unit 32, the blood pressure calculation units 33A to 33C, and the control instruction generation units 34A and 34B) may be implemented by logic circuits (hardware) formed in an integrated circuit (IC chip) and the like, or may be implemented by software using a Central Processing Unit (CPU).

In the latter case, the pulse wave detection devices 2A to 2F and the biometric information generation devices 3A to 3D include a CPU configured to execute instructions of a program as software for implementing each function, a Read Only Memory (ROM) or a storage device (each of these is referred to as "recording medium") in which the program and various types of data are recorded in a computer-readable (or CPU-readable) manner, a Random Access Memory (RAM) in which the program is loaded, and the like. Then, the computer (or CPU) reads out the program from the recording medium and executes the program to achieve the object of the present disclosure. As the recording medium, a "non-transitory tangible medium", such as a tape, a disk, a card, a semiconductor memory, and a programmable logic circuit may be used. Further, the program may be supplied to the computer via any transmission medium (communication network, broadcast wave, or the like) capable of transmitting the program. Note that an aspect of the present disclosure may be implemented in a form of data signal set in a carrier wave, in which the above-mentioned program is embodied by electronic transmission.

Supplement

A pulse wave detection device (2A to 2F) according to a first aspect of the present disclosure is a pulse wave detection device configured to detect a pulse wave of a living body by analyzing an image obtained by capturing the living body, the pulse wave detection device including: an imaging unit (camera 10A to 10C) configured to capture an image of the living body a plurality of times through a first filter (first green filter 12, near-infrared light filter 14) having light transmission characteristics in a near-infrared light wavelength range within a wavelength range where a light absorption coefficient of oxidized hemoglobin is greater than a light absorption coefficient of reduced hemoglobin; and an image analysis unit (20A to 20C) configured to analyze a plurality of images of the living body captured by the imaging unit and to detect the pulse wave of the living body. The image analysis unit is configured to detect the pulse wave by detecting a change in intensity of light in the near-infrared light wavelength range indicated by the plurality of images.

According to the configuration described above, the image analysis unit detects a change in the intensity of the light in the near-infrared light wavelength range indicated by the plurality of images of the living body captured through the first filter having light transmission characteristics in the near-infrared light wavelength range. Here, the intensity of the light in the near-infrared light wavelength range includes not only information on capillary vessels present near the epidermis of the living body, but also information on blood vessels deep in the living body such as an arteriole, and the arteriole contracts and relaxes in accordance with the autonomic nerve of the living body so that the volume flow of blood therein changes. Accordingly, the pulse wave detection device can accurately detect the pulse waves of the living body.

The pulse wave detection device (2A to 2F) according to a second aspect of the present disclosure may be configured such that, in the first aspect, the imaging unit is configured to capture an image of the living body a plurality of times through a second filter (first green filter 12, second green filter 15, cyan filter 16) having light transmission characteristics in a visible light wavelength range within a wavelength range where a light absorption coefficient of oxidized hemoglobin is greater than a light absorption coefficient of reduced hemoglobin, and the image analysis unit is configured to detect the pulse wave using an image captured through the second filter along with the image captured through the first filter.

According to the configuration described above, the pulse wave is detected using, along with the image captured through the first filter, the image captured through the second filter having light transmission characteristics in the visible light wavelength range. With this, since the pulse wave of the living body is detected further taking the information on capillary vessels in the epidermal surface into consideration, the pulse wave of the living body can be more accurately detected.

The pulse wave detection device (2D) according to a third aspect of the present disclosure may be configured such that, in the second aspect, the imaging unit includes a filter (second green filter 15) having light transmission characteristics in a green wavelength range as the second filter.

According to the configuration described above, the pulse wave can be detected using images captured through a filter having light transmission characteristics in the green wavelength range within a wavelength range where the light absorption coefficient of oxidized hemoglobin is greater than the light absorption coefficient of reduced hemoglobin.

The pulse wave detection device (2E) according to a fourth aspect of the present disclosure may be configured such that, in the second aspect, the imaging unit includes a filter (cyan filter 16) having light transmission characteristics in a cyan wavelength range as the second filter.

According to the configuration described above, the pulse wave can be detected using images captured through a filter having light transmission characteristics in the cyan wavelength range within a wavelength range where the light absorption coefficient of oxidized hemoglobin is greater than the light absorption coefficient of reduced hemoglobin.

The pulse wave detection device (2A to 2F) according to a fifth aspect of the present disclosure may be configured such that, in any one of the first to fourth aspects, the image analysis unit is configured to specify a facial region of the living body in the image of the living body and to detect a pulse wave of the living body from at least part of the facial region.

According to the configuration described above, the image analysis unit can detect a pulse wave in the facial region, using the image of the living body.

It is preferable that the pulse wave detection device (2A to 2F) according to a sixth aspect of the present disclosure be configured such that, in the fifth aspect, at least part of the facial region includes at least one of a nose, a forehead, and a cheek of the living body.

According to the above configuration, since there are arteries in the nose, forehead, and cheek of the living body, the pulse wave can be detected more accurately.

It is preferable that the pulse wave detection device (2C) according to a seventh aspect of the present disclosure be configured to further include, in any one of the first to sixth aspects, an irradiation device (near-infrared light irradiation device 19) configured to emit near-infrared light.

According to the above-described configuration, since near-infrared light is emitted by the irradiation device, it is possible to detect, with the imaging unit, a large amount of reflected light of the near-infrared light allowed to be transmitted deep in the living body. As a result, the pulse wave can be detected with higher accuracy.

A biometric information generation system (1A to 1G) according to an eighth aspect of the present disclosure includes the pulse wave detection device according to any one of the first to seventh aspects and a biometric information generation device (3A to 3D) configured to generate biometric information on the living body on the basis of a pulse wave of the living body detected by the pulse wave detection device.

According to the above configuration, the biometric information generation system can generate biometric information on the living body more accurately on the basis of the detailed pulse wave detected by the above pulse wave detection device.

The biometric information generation system (1C) according to a ninth aspect of the present disclosure may be configured such that, in the eighth aspect, the biometric information generation system further includes an electrocardiographic signal detection device (5) configured to detect an electrocardiographic signal and the biometric information generation device (3C) configured to generate the biometric information on the basis of the electrocardiographic signal detected by the electrocardiographic signal detection device and the pulse wave of the living body detected by the pulse wave detection device.

According to the configuration described above, a pulse wave propagation time is calculated on the basis of the pulse wave detected by the pulse wave detection device and the electrocardiographic signal detected by the electrocardiographic signal detection device, and then the biometric information is generated using the pulse wave propagation time. This makes it possible to generate the biometric information more accurately.

The biometric information generation system (1B) according to a tenth aspect of the present disclosure may be configured, in the eighth aspect, to further include a ranging sensor (4) and to generate the biometric information on the basis of a distance detected by the ranging sensor and the pulse wave detected by the pulse wave detection device.

According to the configuration described above, a pulse wave velocity is calculated on the basis of the pulse wave detected by the pulse wave detection device and the distance detected by the ranging sensor, and the biometric information is generated using the pulse wave velocity. This makes it possible to generate the biometric information more accurately.

The biometric information generation system (1A to 1G) according to an eleventh aspect of the present disclosure is such that, in any one of the eighth to tenth aspects, the biometric information may be information associated with at least one of a heart rate, a blood pressure, and a stress level.

The biometric information generation system (1A to 1G) according to a twelfth aspect of the present disclosure is such that, in any one of the eighth to eleventh aspects, the biometric information generation device may be configured to include a control instruction generation unit (34A, 34B) configured to generate a control instruction for controlling another device on the basis of the biometric information.

According to the above configuration, another device can be operated in response to a situation of the living body.

An image analysis device (image analysis units 20A to 20C) according to a thirteenth aspect of the present disclosure is an image analysis device configured to detect a pulse wave of a living body by analyzing an image obtained by capturing the living body, the image analysis device including: an acquisition unit (detection region setting units 21A and 21B) configured to acquire a plurality of images obtained by capturing the living body through a first filter having light transmission characteristics in a near-infrared light wavelength range within a wavelength range where a light absorption coefficient of oxidized hemoglobin is greater than a light absorption coefficient of reduced hemoglobin; and an image analysis unit (the detection region setting units 21A and 21B, pixel value calculation units 22A and 22B, and pulse wave detection units 23A and 23B) configured to analyze the plurality of images of the living body acquired by the acquisition unit and to detect the pulse wave of the living body. The image analysis unit is configured to detect the pulse wave by detecting a change in intensity of light in the near-infrared light wavelength range indicated by the plurality of images.

According to the configuration described above, the image analysis unit detects a change in the intensity of the light in the near-infrared light wavelength range indicated by the plurality of images of the living body captured through the first filter having light transmission characteristics in the near-infrared light wavelength range. Here, the intensity of the light in the near-infrared light wavelength range includes not only information on capillary vessels present near the epidermis of the living body, but also information on blood vessels deep in the living body such as an arteriole, and the arteriole contracts and relaxes in accordance with the autonomic nerve of the living body so that the volume flow of blood therein changes. Accordingly, the image analysis device can accurately detect the pulse wave of the living body.

The image analysis device (image analysis unit 20C) according to a fourteenth aspect of the present disclosure is an image analysis device configured to detect a pulse wave of a living body by analyzing an image obtained by capturing the living body, the image analysis device including: an image analysis unit (detection region setting units 21A and 21B, pixel value calculation units 22A and 22B, and pulse wave detection units 23A and 23B) configured to detect a pulse wave of the living body by analyzing an image obtained by capturing the living body; and a correction unit (pulse wave correction unit 24) configured to correct the pulse wave detected by the image analysis unit on the basis of a motion of the living body detected by a motion sensor configured to detect the motion of the living body.

According to the above-described configuration, since the pulse wave detected by the image analysis unit can be corrected by the correction unit on the basis of the motion of the living body detected by the motion sensor, the pulse wave of the living body can be detected with high accuracy.

A biometric information generation system (1G) according to a fifteenth aspect of the present disclosure includes an imaging device (camera 10A) configured to capture an image of a living body, a motion sensor (6) configured to detect a motion of the living body, the image analysis device according to the fourteenth aspect, and a biometric information generation device (3D) configured to generate biometric information on the living body on the basis of a pulse wave detected by the image analysis device.

According to the above configuration, the biometric information generation system can generate the biometric information on the living body more accurately on the basis of the detailed pulse wave detected by the image analysis device.

It is preferable that the biometric information generation system (1G) according to a sixteenth aspect of the present disclosure be configured such that, in the fifteenth aspect, the biometric information generation device includes a control instruction generation unit (34B) configured to generate a control instruction for controlling another device on the basis of the motion detected by the motion sensor and the biometric information.

According to the above configuration, by using both the information appearing outside the body of the living body and the information inside the body of the living body, the control instruction for controlling another device can be generated. As a result, other devices can be operated in accordance with situations of the living body.

The pulse wave detection device and the biometric information generation device according to each aspect of the present disclosure may be implemented by a computer. In this case, a control program of the pulse wave detection device or the biometric information generation device that causes the computer to function as each unit (software module) included in the pulse wave detection device or the biometric information generation device so as to implement the pulse wave detection device or the biometric information generation device by the computer, and a computer-readable recording medium having stored therein the control program, fall within the scope of the present disclosure.

The present disclosure is not limited to each of the above-described embodiments. It is possible to make various modifications within the scope of the claims. An embodiment obtained by appropriately combining technical elements each disclosed in different embodiments falls also within the technical scope of the present disclosure. Furthermore, technical elements disclosed in the respective embodiments may be combined to provide a new technical feature.

CROSS-REFERENCE TO RELATED APPLICATIONS

This application claims the benefit of priority to Japanese Patent Application Number 2016-219887 filed on Nov. 10, 2016. The entire contents of the above-identified application are hereby incorporated by reference.

REFERENCE SIGNS LIST 1A to 1G Biometric information generation system
2A to 2F Pulse wave detection device
3A to 3D Biometric information generation device
4 Ranging sensor
5 Electrocardiographic signal detection device
6 Motion sensor
10A to 10C Camera (Imaging unit, Imaging device)
12 First green filter (First filter, Second filter)
14 Infrared light filter (First filter)
15 Second green filter (Second filter)
16 Cyan filter (Second filter)
19 Near-infrared light irradiation device (Irradiation device)
20A to 20C Image analysis unit (Image analysis device)
21A, 21B Detection region setting unit (Acquisition unit, Image analysis unit)
22A, 22B Pixel value calculation unit (Image analysis unit)
23A, 23B Pulse wave detection unit (Image analysis unit)
24 Pulse wave correction unit (Correction unit)
34A, 34B Control instruction generation unit
90 External device (another device)

The invention claimed is:
1. An image analysis device configured to detect a pulse wave of a living body by analyzing an image obtained by capturing the living body, the image analysis device comprising:

an acquisition unit configured to acquire a plurality of images obtained by capturing the living body through a first filter having light transmission characteristics in a near-infrared light wavelength range within a wavelength range where a light absorption rate of oxidized hemoglobin is greater than a light absorption rate of reduced hemoglobin, or having light transmission characteristics in a visible light wavelength range and a near-infrared light wavelength range within a wavelength range where a light absorption coefficient of oxidized hemoglobin is greater than a light absorption coefficient of reduced hemoglobin, and through a second filter having light transmission characteristics in a visible light wavelength range and a near-infrared light wavelength range within a wavelength range where a light absorption coefficient of oxidized hemoglobin is greater than a light absorption coefficient of reduced hemoglobin; and an image analysis unit configured to analyze the plurality of images of the living body acquired by the acquisition unit and to detect the pulse wave of the living body, wherein the image analysis unit is configured to detect the pulse wave by using an image captured through the first filter and an image captured through the second filter, the image analysis device includes a correction unit configured to correct the pulse wave detected by the image analysis unit on the basis of a motion of the living body detected by a motion sensor configured to detect the motion of the living body, and the correction unit is configured to correct the pulse wave with a correction amount of pulse waves associated with a specific motion of the living body.

2. A biometric information generation system comprising:
an imaging device configured to capture an image of a living body;
a motion sensor configured to detect a motion of the living body;
the image analysis device according to claim 1; and
a biometric information generation device configured to generate biometric information of the living body on the basis of a pulse wave detected by the image analysis device.

3. The biometric information generation system according to claim 2,
wherein the biometric information generation device includes a control instruction generation unit configured to generate a control instruction for controlling another device on the basis of the motion detected by the motion sensor and the biometric information.

* * * * *